United States Patent [19]
Chen et al.

[11] Patent Number: 5,972,939
[45] Date of Patent: Oct. 26, 1999

[54] CYCLOPENTENE DERIVATIVES USEFUL AS ANTAGONISTS OF THE MOTILIN RECEPTOR

[75] Inventors: Robert H. Chen, Belle Mead; Min Xiang, Bridgewater; John B. Moore, Jr., Neshanic Station, all of N.J.; Mary Pat Beavers, New Hope, Pa.

[73] Assignee: Ortho-McNeil Pharmaceutical, Inc., Raritan, N.J.

[21] Appl. No.: 09/179,135

[22] Filed: Oct. 26, 1998

Related U.S. Application Data

[60] Provisional application No. 60/063,669, Oct. 28, 1997.
[51] Int. Cl.$^6$ .................. A61K 31/16; A61K 31/535; C07C 233/34; C07D 295/14
[52] U.S. Cl. .................. 514/237.8; 514/617; 514/628; 544/86; 544/131; 544/146; 544/148; 544/168; 544/169; 544/159; 544/167; 544/165; 546/190; 546/234; 548/574; 560/45; 564/154; 564/157; 564/158; 564/185; 564/211; 564/212; 564/213

[58] Field of Search .................. 544/168, 169; 564/185, 211; 514/237.8

[56] References Cited

U.S. PATENT DOCUMENTS 4,935,053  6/1990  Burgoyne et al. .................. 564/211

OTHER PUBLICATIONS

Beckert et al, Chemical Abstracts, vol. 128, No. 34728, 1997.

*Primary Examiner*—Robert W. Ramsuer
*Attorney, Agent, or Firm*—Kenneth J. Dow

[57] ABSTRACT

The compounds of formula I are useful in treating gastrointestinal disorders associated with antagonizing the motilin receptor disorders. The compounds compete with erythromycin and motilin for the motilin receptor. In addition the compounds are antagonists of the contractile smooth muscle response to those ligands.

9 Claims, No Drawings

CYCLOPENTENE DERIVATIVES USEFUL AS ANTAGONISTS OF THE MOTILIN RECEPTOR

CROSS REFERENCE TO RELATED APPLICATION

This application claims the priority of provisional application Ser. No. 60/063,669, filed Oct. 28, 1997.

FIELD OF THE INVENTION

This invention relates to a series of novel cyclopentene derivatives, pharmaceutical compositions containing them and intermediates used in their manufacture. The compounds of the invention are useful as non-peptidyl antagonists of the motilin receptor. In addition, the compounds display efficacy and potency which are comparable to known motilin and erythromycin antagonists.

BACKGROUND

In mammals, the digestion of nutrients and the elimination of waste is controlled by the gastrointestinal system. This system is, to say the least, complicated. There are a number of natural peptides, ligands, enzymes, and receptors which play a vital role in this system and are potential targets for drug discovery. Modifying the production of, or responses to these endogenous substances can have an effect upon the physiological responses such as diarrhea, nausea, and abdominal cramping. One example of an endogenous substance which affects the gastrointestinal system is motilin.

Motilin is a peptide of 22 amino acids which is produced in the gastrointestinal system of number of species. Although the sequence of the peptide varies from species to species, there are a great deal of similarities. For example, human motilin and porcine motilin are identical; while motilin isolated from the dog and the rabbit differ by five and four amino acids respectively. Motilin induces smooth muscle contractions in the stomach tissue of dogs, rabbits, and humans as well as in the colon of rabbits. Apart from local gastrointestinal intestinal tissues, motilin and its receptors have been found in other areas. For example motilin has been found in circulating plasma, where a rise in the concentration of motilin has been associated with gastric effects which occur during fasting in dogs and human. Itoh, Z. et al. *Scand. J. Gastroenterol.* 11:93–110, (1976); Vantrappen, G. et al. *Dig. Dis Sci* 24, 497–500 (1979). In addition, when motilin was intravenously administered to humans it was found to increase gastric emptying and gut hormone release. Christofides, N. D. et al. *Gastroenterology* 76:903–907, 1979.

Aside from motilin itself, there are other substances which are agonists of the motilin receptor and which elicit gastrointestinal emptying. One of those agents is the antibiotic erythromycin. Even though erythromycin is a useful drug, a great number of patients are affected by the drug's gastrointestinal side effects. Studies have shown that erythromycin elicits biological responses that are comparable to motilin itself and therefore may be useful in the treatment of diseases such as chronic idiopathic intestinal pseudo-obstruction and gastroparesis. Weber, F. et al., *The American Journal of Gastroenterology*, 88:4, 485–90 (1993).

Although motilin and erythromycin are agonists of the mtotilin receptor, there is a need for antagonists of this receptor as well. The nausea, abdominal cramping, and diarrhea which are associated with motilin agonsits are not always welcome physiological events. The increased gut motility induced by motilin has been implicated in diseases such as Irritable Bowel Syndrome and esophageal reflux. Therefore researchers have been searching for motilin antagonists.

One such antagonist is OHM-11526. This is a peptide derived from porcine motilin which competes with both motilin and erythromycin for the motilin receptor in a number of species, including rabbits and humans. In addition, this peptide is an antagonist of the contractile smooth muscle response to both erythromycin and motilin in an in vitro rabbit model. Depoortere, I. et al., *European Journal of Pharmacology*, 286, 241–47, (1995). Although this substance is potent in that model ($IC_{50}$ 1.0 nm) it is a peptide and as such offers little hope as an oral drug since it is susceptible to the enzymes of the digestive tract. Zen Itoh, *Motilin*, xvi (1990). Therefore it is desirable to find other agents which are not peptides as potential motilin antagonists. The compounds of this invention are such agents.

The compounds of this invention are non-peptidyl motilin antagonists with potencies and activities comparable to known peptidyl motilin antagonists. These compounds compete with motilin and erythromycin for the motilin receptor site in vitro. In addition, these compounds suppress smooth muscle contractions induced by motilin and erythomycin with activities and potencies comparable to OHM 11526 in an in vitro model.

SUMMARY OF THE INVENTION

The present invention is directed to compounds of Formula I

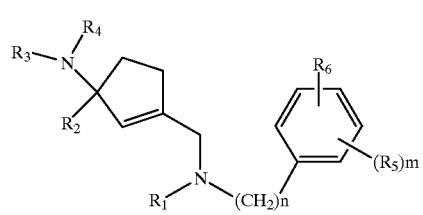

wherein $R_1$ is hydrogen, $C_{1-5}$alkyl, substituted $C_{1-5}$alkyl (where the alkyl substituents are one or more halogens), amino$C_{1-5}$alkyl, $C_{1-5}$alkylamino$C_{1-5}$alkyl; di-$C_{1-5}$-salkylamino$C_{1-5}$alkyl, $R_aR_bN$-$C_{1-5}$alkyl (where the $R_a$ and $R_b$ are independently selected from hydrogen and $C_{1-5}$alkyl, or are taken together to form a morpholine, piperazine, piperidine, or N-substituted piperidine where the N-substitutent is $C_{1-5}$alkyl or phenyl$C_{1-5}$alkyl), $C_{1-5}$alkylcarbonyl, $C_{1-5}$alkoxycarbonyl, aminocarbonyl, $C_{1-9}$alkylaminocarbonyl, cyclo$C_{3-9}$alkylaminocarbonyl, pyridinylcarbonyl, substituted pyridinylcarbonyl (where the pyridinyl substituents are selected from the group consisting of one or more halogens and $C_{1-5}$alky), thiophenecarbonyl, substituted thiophenecarbonyl (where the thiophene substituents are) selected from the group consisting of one or more halogens and $C_{1-5}$alkyl), phenyl, phenyl$C_{1-5}$alkyl, phenoxycarbonyl, phenylcarbonyl, diphenylmethylcarbonyl, phenylaminocarbonyl, phenylthiocarbonyl, phenylaminothiocarbonyl, substituted phenyl, substituted phenyl$C_{1-5}$alkyl, substituted phenoxycarbonyl, substituted phenylcarbonyl, substituted phenylaminocarbonyl, substituted diphenylmethylcarbonyl, substituted phenylthiocarbonyl, and substituted phenylaminothiocarbonyl (where the phenyl substituents are selected from the group consisting of one or more of halogen, $C_{1-5}$alkyl, trihalomethyl, $C_{1-5}$alkoxy, amino, nitrile, nitro, $C_{1-5}$alkylamino, di-$C_{1-5}$salkylamino, if there are more than one substitutents they may be taken together with the phenyl ring to form a fused bicyclic 7–10 membered heterocyclic ring having one to two heteroaloms selected from oxygen, sulfur or nitrogen or the substituents may be taken together to form a fused bicyclic 7–10 membered aromatic ring;

$R_2$ is hydrogen, $C_{1-5}$alkyl, $C_{1-5}$ralkoxy, phenyl, substituted phenyl (where the phenyl substituents are selected from one or more of the group consisting of halogen and $C_{1-5}$alkyl), phenyl$C_{1-5}$alkyl, substituted phenyl$C_{1-5}$alkyl (where the phenyl substituents are selected from one or more of the group consisting of halogen, $C_{1-5}$alkyl, $C_{1-5}$alkoxy, halo and di-$C_{1-5}$alkylamino)

$R_3$ is hydrogen, $C_{1-5}$alkylcarbonyl, substituted $C_{1-5}$alkylcarbonyl (where the alkyl substituents are selected from one or more halogens), phenylcarbonyl, and substituted phenylcarbonyl (where the phenyl substituents are selected from one or more of the group consisting of halogen, $C_{1-5}$alkyl, $C_{1-5}$alkoxy, amino, $C_{1-5}$alkylamino, and di-$C_{1-5}$alkylamino)

$R_4$ is hydrogen, $C_{1-5}$alkylcarbonyl, substituted $C_{1-5}$alkylcarbonyl (where the alkyl substituents are selected from one or more halogens), phenylcarbonyl, and substituted phenylcarbonyl (where the phenyl substituents are selected from one or more of the group consisting of halogen, $C_{1-5}$alkyl, $C_{1-5}$alkoxy, amino, $C_{1-5}$alkylamino, and di-$C_{1-5}$alkylamino)

n is 0–3;
m is 1–5
$R_5$ is

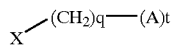

where:
q is 0–2;
t is 0–1;
X is oxygen, $CH_2$, sulfur, or $NR_c$ where
  $R_c$ is hydrogen, $C_{1-5}$alkyl, morpholino$C_{1-5}$alkyl, piperidinyl$C_{1-5}$alkyl, N-phenylmethylpiperidinyl or piperazinyl$C_{1-5}$alkyl,
with the proviso that if q and t are 0, then X is hydroxy, thiol, or amino,
A is $C_{1-5}$salkoxycarbonyl, phenylcarbonyl, or $R_7R_8N$—
  where $R_7$ is independently selected from hydrogen, $C_{1-5}$alkyl, cyclo$C_{3-9}$alkyl, or $R_7$ is taken together with $R_8$ to form a 5 or 6 membered heterocyclic ring with one or more heteroatoms selected from the group consisting of oxygen, nitrogen or sulfur and N-oxide.s thereof;
    $R_8$ is independently selected from hydrogen, $C_{1-5}$alkyl, cyclo$C_{3-9}$galkyl or taken together with $R_7$ to form a 5 or 6 membered heterocyclic ring with one or more heteroatoms selected from the group consisting of oxygen, nitrogen or sulfur, and N-oxides thereof;
$R_6$ is hydrogen, halogen, $C_{1-5}$alkoxy, $C_{1-5}$alkylamino, or di-$C_{1-5}$alkylamino or pharmaceutically acceptable salts thereof.

The compounds of formula I are useful in treating gastrointestinal disorders associated with the motilin receptor. The compounds compete with erythromycin and motilin for the motilin receptor. In addition, the compounds are antagonists of the contractile smooth muscle response to those ligands.

The present invention also comprises pharmaceutical compositions containing one or more of the compounds of formula I as well as methods for the treatment of disorders related to the gastrointestinal system which are associated with the motilin receptor. Such diseases include Irritable Bowel Syndrome, esophageal reflux, and the gastrointestinal side effects of erythromycin.

DETAILED DESCRIPTION OF THE INVENTION

The terms used in describing the invention are commonly used and known to those skilled in the art. However, the terms that could have other meanings are defined. "Independently" means that when there are more than one substituent, the substituents may be different. The term "alkyl" refers to straight, cyclic and branched-chain alkyl groups and "alkoxy" refers O-alkyl where alkyl is as defined supra. The symbol "Ph" refers to phenyl, the term "fused bicyclic aromatic" includes fused aromatic rings such as naphthyl and the like. The term "fused bicyclic heterocycle" includes benzodioxoles and the like.

Since the compounds of the invention have a chiral center, some of the compounds are isolated as enantiomers. In those cases the determination of absolute stereochemistry is pending.

When compounds contain a basic moiety, acid addition salts may be prepared and may be chosen from hydrochloric, hydrobromic, hydroiodic, perchloric, sulfuric, nitric, phosphoric, acetic, propionic, glycolic, lactic, pyruvic, oxalic, malonic, succinic, maleic, fumaric, malic, tartaric, citric, benzoic, cinnamic, mandelic, methanesulfonic, p-toluenesulforlic, cyclohexanesulfamic, salicylic, 2-phenoxybenzoic, 2-acetoxybenzoic, or saccharin, and the like. Such salts can are made by reacting the free base of compounds of formula I with the acid and isolating the salt.

The compounds of the invention may be prepared by the following schemes, where some schemes produce more than one embodiment of the invention. In those cases, the choice of scheme is a matter of discretion which is within the capabilities of those skilled in the art.

A synthesis of the compounds of the invention is depicted in Scheme 1. Essentially this scheme assembles two halves of the molecule and couples them. For one half, 3-ethoxy-2-cyclohexen-1-one,1a, is the starting material. 1a is treated with a Grignard reagent, 1b, such as 4-fluorobenzyl magnesium bromide at room temperature under an inert atmosphere, using ether as a solvent to give the α,β-unsaturated ketone derivative 1c. Treatment of 1c with a reducing agent such as LAH at 0° C. to room temperature over 16 h gives the alcohol, 1d. This alcohol is treated with a strong base such as NaH and trichloroacetonitrile from 0° C. to room temperature for 16 h to give the amide 1e. This six membered ring amide is sequentially treated with ozone at −78° C., dimethylsulfide, and a catalytic amount of acid such as toluene sulfonic acid. Once addition is complete, the mixture is allowed to warm to room temperature over 24–64 h to give the five membered ring aldehyde 1f, as a racemic mixture.

To assemble the other half, an aromatic alcohol 1g, such as 3-hydroxyaniline is treated with a mild base, such as $K_2CO_3$, in a suitable solvent such as EtOH at 60° C. over 4–6 h. This mixture is subsequently treated with a halide derivative 1h, such as 3-chloropropylmorpholine at room temperature to give the amine 1i. This amine is treated with the aldehyde 1f and $NaCNBH_3$ in MeOH at room temperature over 30 min to give a compound of the invention, 1j as a racemic mixture.

If pure enantiomers are desired, they may be obtained in any of three stages of the synthesis. The alcohol 1d, the aldehyde 1f, and the product 1j may all be separated via HPLC using chiral columns or methods known of those skilled in the art. With respect to all three compounds, they may be further manipulated to give other compounds of the invention without sacrificing their enantiomeric purity. This scheme may be used to produce other compounds of the invention. For example, to produce compounds where X is sulfur, simply replace reagent 1h with an aromatic thiol, such as 3-aminothiophenol and carry out the remaining steps of the Scheme.

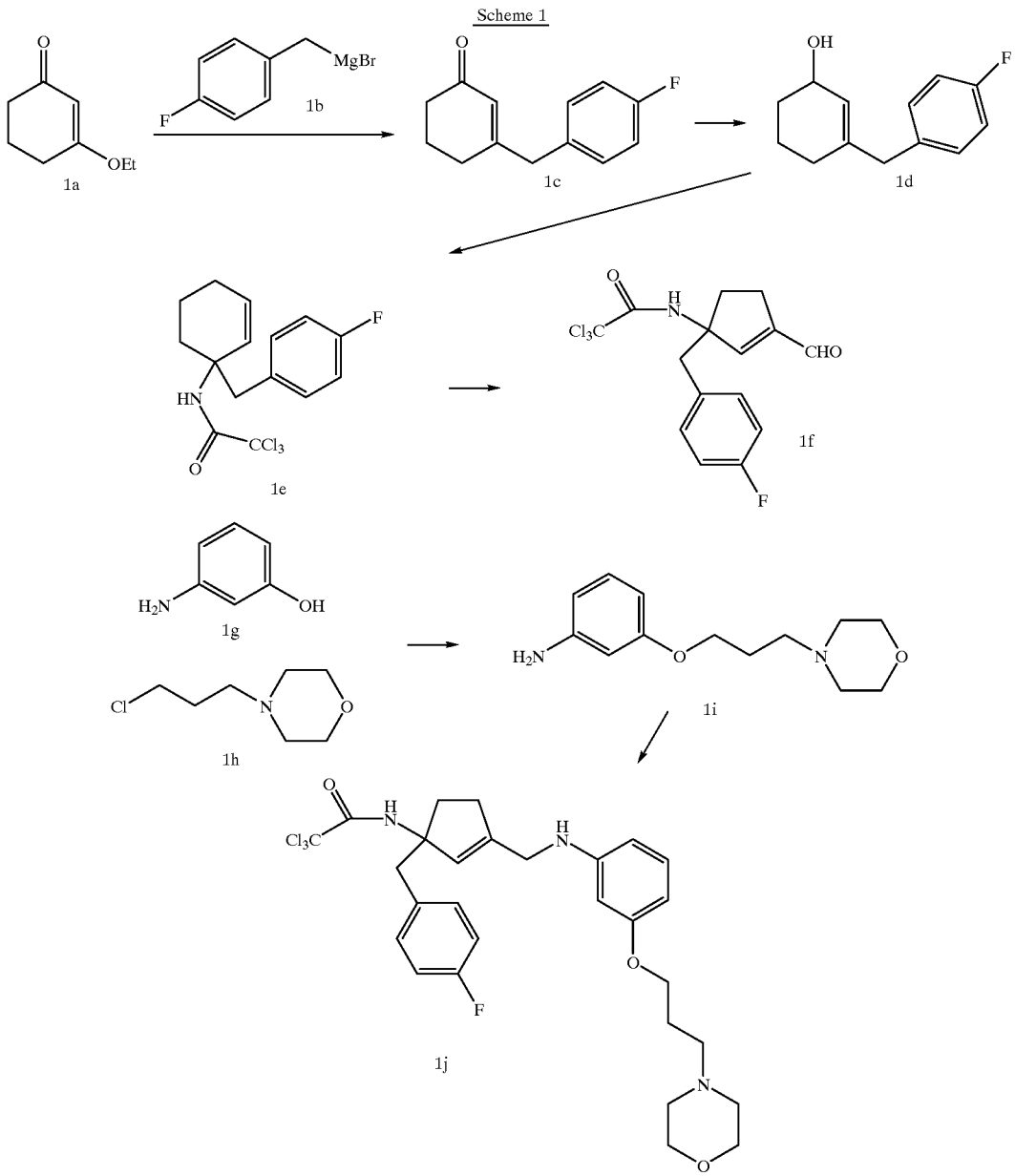

Scheme 1

To produce other substitutions at $R_3$ or $R_4$ some of the products of Scheme 1 may be used. For example, to produce a compound where $R_3$ is hydrogen and $R_4$ is $CH_3C(O)—$, the six-membered ring intermediate 1e, is treated with a base, such as barium hydroxide, at reflux in EtOH to give the free amine 2a. The amine is subsequently treated with an acid anhydride, such as trifluoroacetic anhydride to give 2b. This intermediate may be carried through the remaining steps of Scheme 1 to produce the desired compound.

Scheme 2

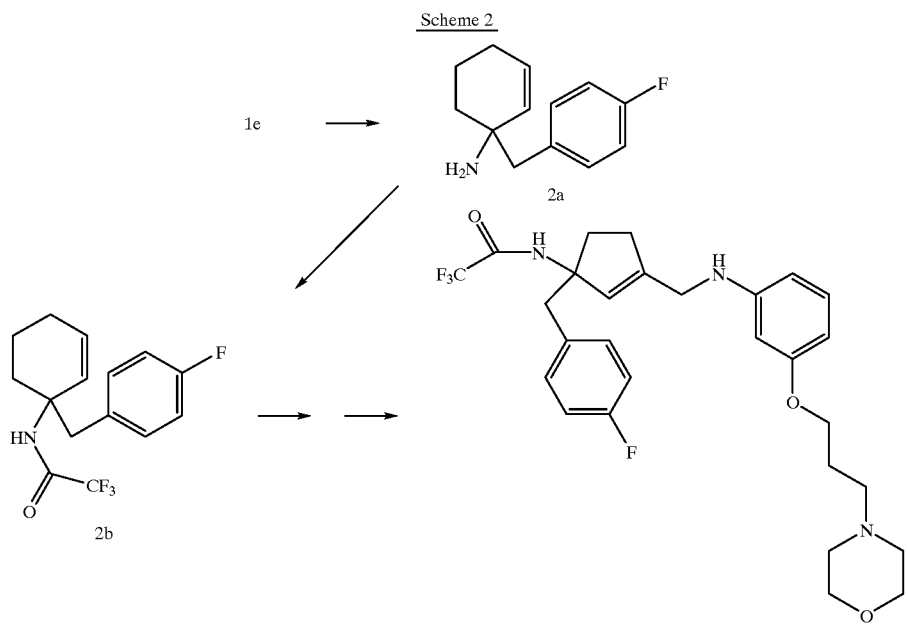

The products of Scheme 1 may be used to produce other compounds of the invention. For example, to produce compounds of type 3a, treat compound 1j with a phenyl isocyanate at room temperature over 24 h. To produce compounds of type 3b, 1j may be treated at room temperature with acid chloride derivatives such as benzoyl chloride. In order to produce thiols 3c, compounds of type 1j may be treated with isothiocyanates, such as phenylisothiocyanate at room temperature. As discussed earlier, if pure enantiomers are desired, they may be obtained by chromatography of the reactant, 1j or the products.

Scheme 3

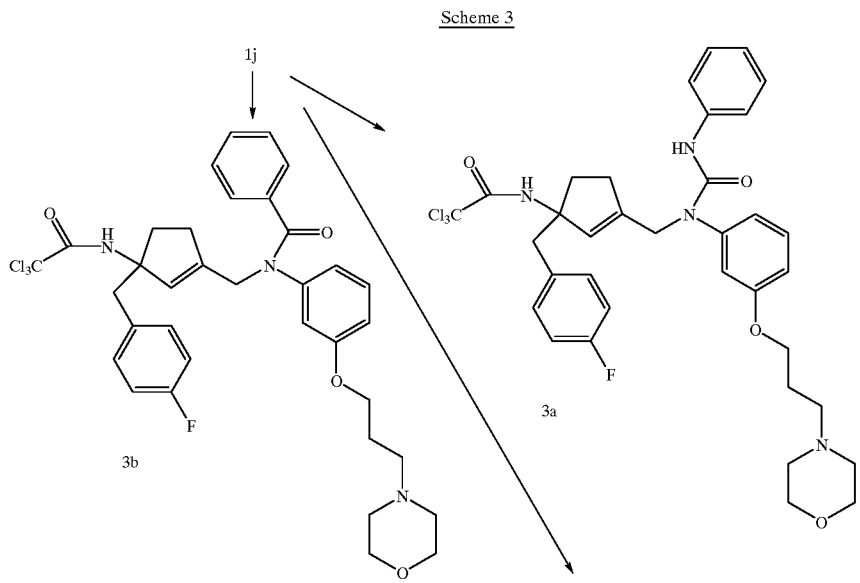

-continued

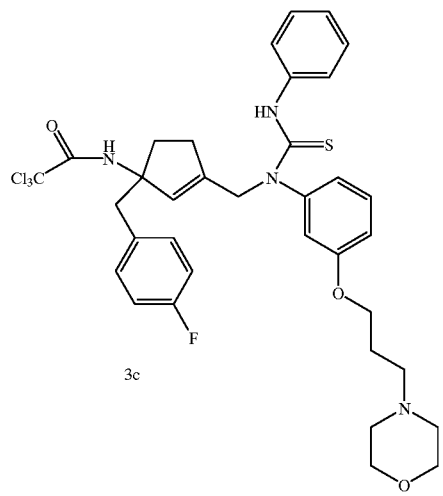

3c

Yet another scheme (Scheme 4) makes use of the intermediate of Scheme 1. Treatment of the aldehyde, 1f, with a nitroaniline derivative 4a, and NaCNBH₃ at room temperature gives the coupled intermediate 4b. This intermediate may be acylated with benzoyl chloride and a mild base such as triethylamine to give the N-acyl intermediate 4c. 4c may be treated with a reducing agent such as Pd/C to give the aniline compound 4d. This compound may be coupled with a halogen derivative 4e, such as 3-chloropropylpiperidine, using DBU and an alcoholic solvent at reflux over 4 h to give a mixture of mono and di amine products.

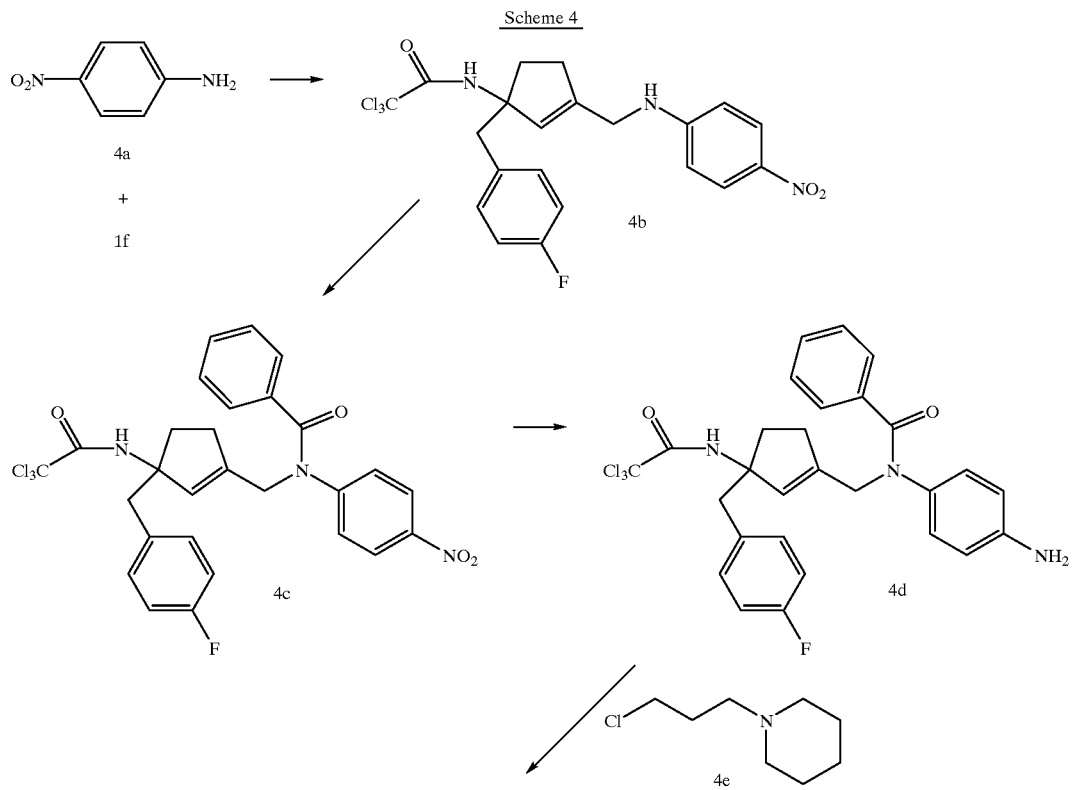

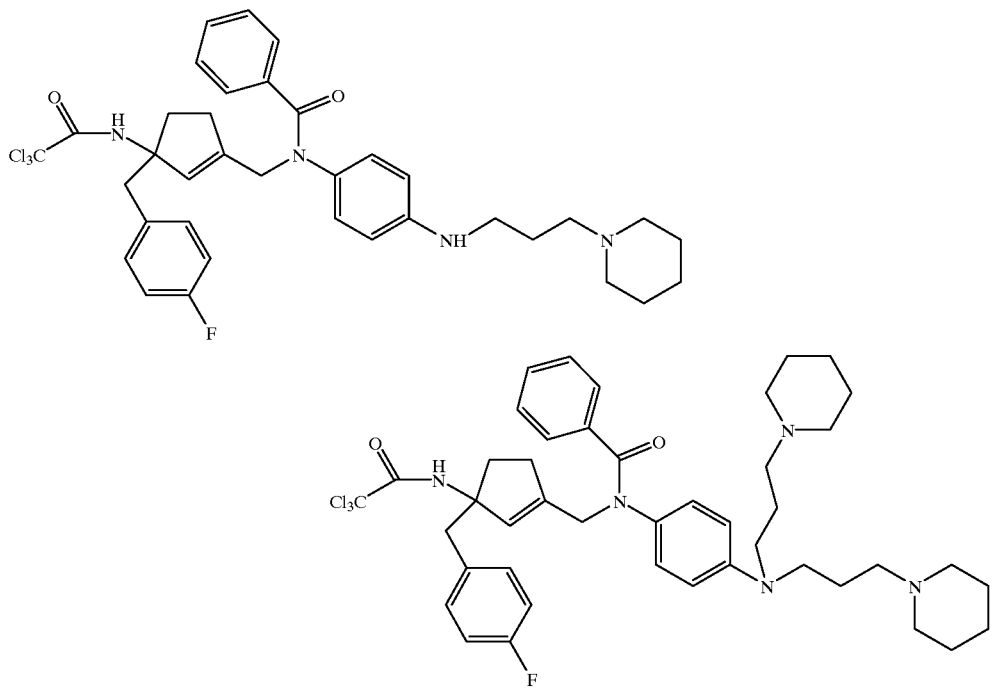

To prepare compounds of the invention where n is 1–3, products of Scheme 1 are used in Scheme 5. Intermediate 1f is treated with 3-(m-hydroxyphenyl)propylamine, an aromatic amino alcohol derivative 5a, and NaCNBH$_3$ at room temperature over 16 h to give the amine 5b. Treatment of 5b with a thiocyanate derivative 5c, and a mild base at room temperature gives the substituted thioamide 5d. This compound may be treated with a halide reagent, 5e, and a base such as DBU in an alcoholic solvent at reflux to give the O-substituted compound of the invention.

Scheme 5

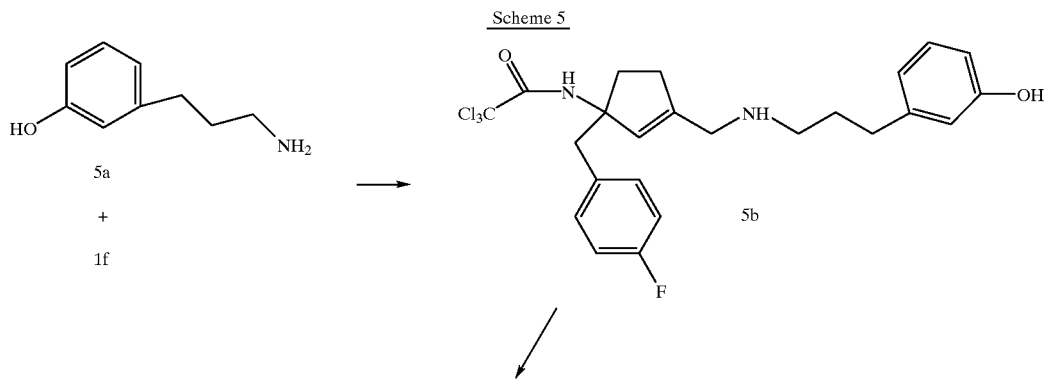

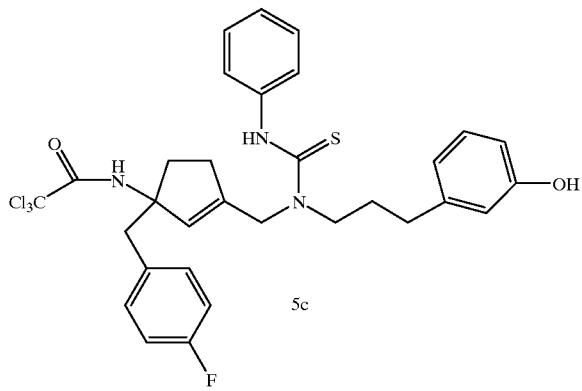

5c

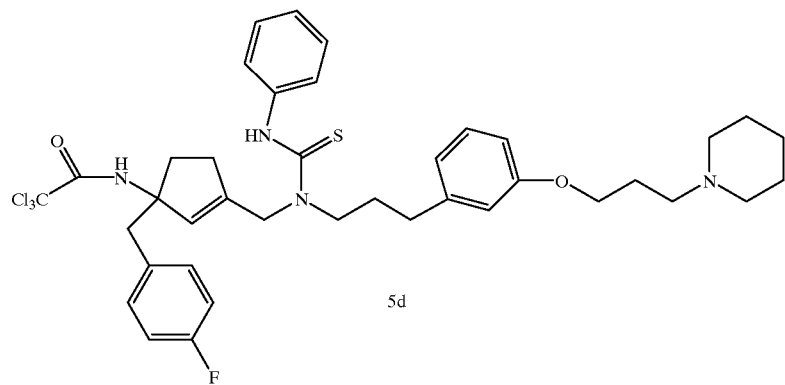

5d

The compounds of the invention were tested for their ability to compete with radiolabeled motilin (porcine) for the motilin receptors located on the colon of mature rabbits. The colon from mature New Zealand rabbits was removed, dissected free from the mucosa and serosa layers, and diced into small pieces. The muscle tissues were homogenized in 10 volumes of buffer (50 mM Tris-Cl, 10 mM $MgCl_2$, 0.1 mg/mL bactracin, and 0.25 mM Peflabloc, pH 7.5) in a Polytron (29,000 rpm, 4×15 seconds). The homogenate was centrifuged at 1000×g for 15 min. and the supernatant discarded. The pellet was washed twice before being suspended in homogenizing buffer. This crude homogenate is then passed first through a 19 gauge needle then a 23 gauge needle to further suspend the material and stored as −80° C. In a total volume of 0.50 mL, the binding assay contains the following components added sequentially, buffer (50 mM Tris-Cl, 10 mM $MgCl_2$, 1 mM EDTA, 15 mg/mL BSA, 5 µg/mL leupeptin, aprotinin, and pepstatin, and 0.1 mg/mL, bactracin), $1_{125}$ motilin (Amersham, ca 50,000–70,000 cpm, 25–40 pM), the test compound (the initial concentration was 2 mM/100% DMSO, which diluted with $H_2O$ to a final concentration of 10 µM) and membrane protein (100–300 µg). After 30 min, at 30° C., the material was cooled on ice and centrifuged at 13,000×g for 1 minute. The pellet was washed with 1 mL 0.9% saline and centrifuged at 13,000×g for 15 seconds. The pellet was washed again with cold saline and the supernatant was removed. The pellet was counted in the gamma counter to determine the percentage of unbound motilin and thereby the percent inhibition of the test compound. $IC_{50s}$ were determined for some compounds by standard techniques.

TABLE A

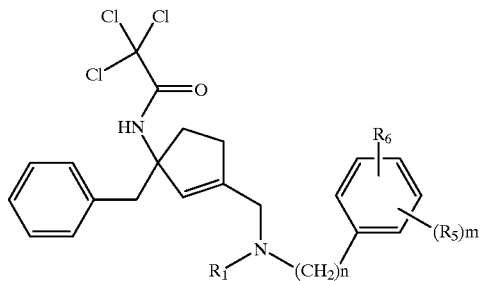

| RWJ/Cpd. | $R_1$ | n | $R_5$ | $R_6$ | $IC_{50}$/% Inhibition |
|---|---|---|---|---|---|
| 8 | phenylNH—C(O) | 0 | 3-O(CH$_2$)$_2$morpholin-1-yl | H | 20 nM** |
| 9 | phenylNH—C(O) | 0 | 3-O(CH$_2$)$_2$morpholin-1-yl | H | >300 nM*** |
| 69 | H | 0 | 4-OH | H | 11% @ 10 μM |
| 50 | (CH$_2$)$_2$NEt$_2$ | 0 | 3-OH | H | 81% @ 10 μM |
| 51 | (CH$_2$)$_2$NEt$_2$ | 0 | 3-O(CH$_2$)$_2$NEt$_2$ | H | 0.6% @ 10 μM |
| 52 | (CH$_2$)$_2$NEt$_2$ | 0 | 3-O(CH$_2$)$_2$piperidin-1-yl | H | 0.6 |
| 53 | (CH$_2$)$_2$NEt$_2$ | 0 | 3-O(CH$_2$)$_2$morpholin-1-yl | H | 0.3 |
| 54 | (CH$_2$)$_2$NEt$_2$ | 0 | 3-O(CH$_2$)$_3$piperidin-1-yl | H | 0.9 |
| 55 | (CH$_2$)$_2$NEt$_2$ | 0 | 3-O(CH$_2$)$_2$pyrrolidin-1-yl | H | 0.9 |
| 70 | (CH$_2$)$_2$NEt$_2$ | 0 | 2-O(CH$_2$)$_2$morpholin-1-yl | H | 80% @ 10 μM |
| 56 | H | 0 | 4-S(CH$_2$)$_2$NMe$_2$ | H | 1.5 |
| 71 | (CH$_2$)$_2$NEt$_2$ | 0 | 4-O(CH$_2$)$_2$NMe$_2$ | H | 85% @ 10 μM |
| 58 | H | 0 | 4-S(CH$_2$)$_2$NEt$_2$ | H | 1.8 |
| 57 | (CH$_2$)$_2$-morpholin-1-yl | 1 | 3-O(CH$_2$)$_2$morpholin-1-yl | H | 0.7 |
| 72 | (CH$_2$)$_2$NEt$_2$ | 0 | 2-O(CH$_2$)$_2$morpholin-1-yl | H | 0.9 |
| 73 | (CH$_2$)$_2$NEt$_2$ | 0 | 2-OH | H | 84% @ 10 μM |
| 74 | (CH$_2$)$_2$NEt$_2$ | 0 | 4-OH | H | 81% @ 10 μM |
| 75 | H | 0 | 3-NH$_2$ | H | 41% @ 10 μM |
| 76 | (CH$_2$)$_2$NEt$_2$ | 2 | 4-OH | H | 84% @ 10 μM |
| 77 | 1-benzylpip-eridin-4-yl | 1 | 3-O(CH$_2$)$_2$NEt$_2$ | H | 0.8 |
| 58 | H | 0 | 3-S(CH$_2$)$_2$NEt$_2$ | H | 61% @ 10 μM |
| 78 | CH$_3$C(O) | 0 | 3-O(CH$_2$)$_2$morpholin-1-yl | H | 1.03 |
| 10 | phenylC(O) | 0 | 3-O(CH$_2$)$_2$morpholin-1-yl | H | 0.3 |
| 6 | H | 0 | 3-O(CH$_2$)$_2$morpholin-1-yl | H | 37% @ 10 μM |
| 46 | phenylC(O) | 0 | 3-OCH$_2$CO$_2$Et | H | 51% @ 10 μM |
| 79 | phenylC(O) | 0 | 3-S(CH$_2$)$_2$NEt$_2$ | H | 98% @ 10 μM |
| 22 | phenylNH—C(O) | 0 | 3-S(CH$_2$)$_2$morpholin-1-yl | H | 83% @ 10 μM |
| 80 | 4-F-phenyl-C(O) | 0 | 3-S(CH$_2$)$_2$morpholin-1-yl | H | 79% @ 10 μM |
| 81 | H | 2 | 3-S(CH$_2$)$_2$morpholin-1-yl | H | 81% @ 10 μM |
| 82 | phenylC(O) | 0 | 3-S(CH$_2$)$_2$morpholin-1-yl | H | 80% @ 10 μM |
| 83 | phenylC(O) | 1 | 3-O(CH$_2$)$_2$NEt$_2$ | H | 100% @ 10 μM |
| 84 | 4-CH$_3$O-phenylC(O) | 0 | 3-S(CH$_2$)$_2$morpholin-1-yl | H | 59% @ 10 μM |
| 85 | (CH$_2$)$_2$-morpholin-1-yl | 2 | 3-O—C(O)phenyl | H | 9% @ 2.0 μM |
| 86 | phenylC(O) | 0 | 4-S(CH$_2$)$_2$N(CH$_3$)$_2$ | H | 49% @ 2.0 μM |
| 40 | H | 0 | 3-O(CH$_2$)$_2$morpholin-1-yl | 4-OCH$_3$ | 27% @ 10 μM |
| 87 | H | 0 | 3-OH | 4-OCH$_3$ | 32% @ 10 μM |
| 88 | benzyl | 1 | 3-O(CH$_2$)$_2$morpholin-1-yl | H | 94% @ 10 μM |
| 89 | 4-CH$_3$O-phenylNH—C(O) | 0 | 3-O(CH$_2$)$_2$morpholin-1-yl | H | 26% @ 5.0 μM |
| 90 | 3-CH$_3$O-phenyl-C(O) | 0 | 3-O(CH$_2$)$_2$morpholin-1-yl | H | 65% @ 0.5 μM |
| 91 | phenylC(O) | 1 | 1-benzylpip-eridin-4-amino | H | 77% @ 10 μM |
| 92 | (CH$_2$)$_2$NEt$_2$ | 2 | 3-O(CH$_2$)$_2$morpholin-1-yl | H | 95% @ 10 μM |
| 32 | phenylC(O) | 1 | 3-O(CH$_2$)$_2$morpholin-1-yl | H | 70% @ 10 μM |
| 59 | 4-F-phenyl-C(O) | 0 | 3-O(CH$_2$)$_2$morpholin-1-yl | H | 52 nM |
| 60 | 4-CH$_3$O-phenyl-C(O) | 0 | 3-O(CH$_2$)$_2$morpholin-1-yl | H | 90 nM |
| 7 | phenylNH—C(O) | 0 | 3-O(CH$_2$)$_2$morpholin-1-yl | H | 45 nM |
| 93 | benzyl | 0 | 3-O(CH$_2$)$_2$morpholin-1-yl | 4-OCH$_3$ | 62% @ 10 μM |
| 94 | H | 0 | 3-O(CH$_2$)$_2$morpholin-1-yl | 4-OCH$_3$ | 48% @ 10 μM |
| 34 | phenylC(O) | 0 | 3-O(CH$_2$)$_2$morpholin-1-yl | 4-OCH$_3$ | 74% @ 10 μM |
| 95 | (CH$_2$)$_2$-morpholin-1-yl | 2 | 3-O—C(O)phenyl | 4-OCH$_3$ | 22% @ 2.0 μM |
| 41 | phenylC(O) | 2 | 3-O(CH$_2$)$_2$morpholin-1-yl | H | 82% @ 10 μM |
| 96 | 4-CH$_3$)$_2$N-phenylC(O) | 2 | 3-O(CH$_2$)$_2$morpholin-1-yl | H | 62% @ 1.0 μM |
| 97 | 3,4-dichlorophenylC(O) | 0 | 3-O(CH$_2$)$_2$morpholin-1-yl | H | 260 nM |
| 98 | 4-F-phenylC(O) | 0 | 3-(CH$_2$)$_3$morpholin-1-yl | H | 17% @ 1.0 μM |
| 99 | 3,5-di-CF$_3$-phenylC(O) | 0 | 3-O(CH$_2$)$_2$morpholin-1-yl | H | 28% @ 1.0 μM |
| 100 | 2,3,4,5,6-pentafluoro-phenylC(O) | 0 | 3-O(CH$_2$)$_2$morpholin-1-yl | H | 1000 nM |
| 19 | phenyl-NHC(O) | 0 | 3-(CH$_2$)$_3$morpholin-1-yl | H | 59% @ 1.0 μM |

TABLE A-continued

| RWJ/Cpd. | R₁ | n | R₅ | R₆ | IC₅₀/% Inhibition |
|---|---|---|---|---|---|
| 61 | 4-Br-phenylC(O) | 0 | 3-O(CH₂)₂morpholin-1-yl | H | 64% @ 0.05 μM |
| 101 | 3-Br-phenylC(O) | 0 | 3-O(CH₂)₂morpholin-1-yl | H | 54% @ 0.1 μM |
| 102 | 4-Cl-phenylC(O) | 0 | 3-O(CH₂)₂morpholin-1-yl | H | 61% @ 0.1 μM |
| 103 | 3-CF₃-phenylC(O) | 0 | 3-O(CH₂)₃morpholin-1-yl | H | 52% @ 0.1 μM |
| 104 | 4-CF₃-phenylC(O) | 0 | 3-O(CH₂)₂morpholin-1-yl | H | 29% @ 0.1 μM |
| 105 | 4-I-phenylC(O) | 0 | 3-O(CH₂)₂morpholin-1-yl | H | 59% @ 0.1 μM |
| 106 | 3,5-di-F₂-phenylC(O) | 0 | 3-O(CH₂)₂morpholin-1-yl | H | 78% @ 0.1 μM |
| 62 | 3,4-di-F₂-phenylC(O) | 0 | 3-O(CH₂)₂morpholin-1-yl | H | 50 nM |
| 1407 | 4-(phenyl)phenylC(O) | 0 | 3-O(CH₂)₂morpholin-1-yl | H | 58% @ 1.0 μM |
| 108 | thiophen-2-yl-C(O) | 0 | 3-O(CH₂)₂morpholin-1-yl | H | 84% @ 1.0 μM |
| 11 | phenylNH—C(S) | 0 | 3-O(CH₂)₂morpholin-1-yl | H | 45% @ 0.1 μM |
| 109 | 4-NC-phenylC(O) | 0 | 3-O(CH₂)₂morpholin-1-yl | H | 98 nM |
| 110 | 4-t-butyl-phenylC(O) | 0 | 3-O(CH₂)₂morpholin-1-yl | H | 19% @ 1.0 μM |
| 111 | pyridin-4-yl-C(O) | 0 | 3-O(CH₂)₂morpholin-1-yl | H | 51% @ 1.0 μM |
| 63 | 3-F-phenyl-NHC(O) | 0 | 3-O(CH₂)₂morpholin-1-yl | H | 37 nM |
| 112 | 3-Br-phenyl-NHC(O) | 0 | 3-O(CH₂)₂morpholin-1-yl | H | 51% @ 1.0 μM |
| 38 | 4-Br-phenyl-C(O) | 0 | 3-O(CH₂)₂morpholin-1-yl | 6-Cl | 59% @ 1.0 μM |
| 113 | 3-F-phenyl-C(O) | 0 | 3-O(CH₂)₂morpholin-1-yl | 6-Cl | 59% @ 1.0 μM |
| 114 | 3,4-diF-phenyl-C(O) | 0 | 3-O(CH₂)₂morpholin-1-yl | 6-Cl | 52% @ 100 μM |
| 115 | 3-Br-thiophen-1-yl-C(O)- | 0 | 3-O(CH₂)₂morpholin-1-yl | H | 65% @ 1.0 μM |
| 116 | 4-NO₂-phenyl-C(O) | 0 | 3-O(CH₂)₂morpholin-1-yl | H | 69% @ 0.1 μM |
| 117 | di-phenyl-CH—C(O) | 0 | 3-O(CH₂)₂morpholin-1-yl | H | 42% @ 1.0 μM |
| 118 | phenyl-OC(O) | 0 | 3-O(CH₂)₂morpholin-1-yl | H | 51% @ 1.0 μM |
| 119 | cyclohexyl-NHC(O) | 0 | 3-O(CH₂)₂morpholin-1-yl | H | 56% @ 1.0 μM |

TABLE B

| Cpd. | R₁ | n | R₂ | IC₅₀/% Inhibition |
|---|---|---|---|---|
| 120 | 4-F-phenyl-NH—C(O) | 0 | 3-Cl-benzyl | 10 nM |
| 121 | 4-F-phenyl-C(O) | 0 | 3-Cl-benzyl | 30 nM |
| 65 | 4-F-phenyl-C(O) | 0 | 4-MeO-benzyl | 56 nM |
| 66 | phenyl-C(O) | 0 | 4-MeO-benzyl | 56 nM |
| 122 | 1,3-benzodioxol-5-yl-C(O) | 0 | benzyl | 77% @ 1.0 μM |
| 123 | phenyl-NH—C(O) | 0 | (CH₃)₂CH— | 51% @ 1.0 μM |
| 124 | naphthy-1-yl-C(O) | 0 | benzyl | 40% @ 0.1 μM |
| 125 | 4-F-phenyl-C(O) | 0 | 4-F-benzyl | 43% @ 0.04 μM |
| 126 | 3-F-phenyl-C(O) | 0 | 4-F-benzyl | 44% @ 0.04 μM |
| 67 | phenyl-NHC(O) | 0 | 4-F-benzyl | 34% @ 0.25 μM |
| 127 | phenyl-NHC(O) | 0 | phenyl | 33% @ 0.1 μM |
| 128 | 4-F-phenyl-C(O) | 0 | phenyl | 43% @ 0.1 μM |
| 68 | phenyl-NHC(O) | 0 | 3-Cl-benzyl | 70% @ 0.1 μM |
| 129 | 4-Br-phenyl-C(O) | 0 | 3-Cl-benzyl | 70% @ 0.1 μM |

TABLE B-continued

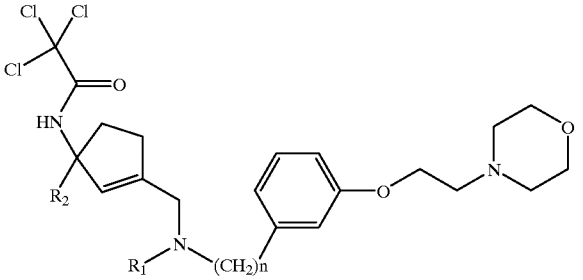

| Cpd. | R₁ | n | R₂ | IC₅₀/% Inhibition |
|---|---|---|---|---|
| 130 | 3,4-di-F-phenyl-C(O) | 0 | 3-Cl-benzyl | 78% @ 0.1 $\mu$M |

TABLE C

| Cpd. | R$_1$ | R$_2$ | R$_3$ | R$_5$ | IC$_{50}$/% Inhibition |
|---|---|---|---|---|---|
| 131 | H | benzyl | CF$_3$C(O) | 3-O(CH$_2$)$_2$morpholin-1-yl | 25% @ 10 $\mu$M |
| 132 | phenyl-C(O) | benzyl | CF$_3$C(O) | 3-O(CH$_2$)$_2$morpholin-1-yl | 0.73 nM |
| 15 | phenyl-NH–C(O) | benzyl | CH$_3$C(O) | 3-O(CH$_2$)$_2$morpholin-1-yl | 40% @ 1.0 $\mu$M |
| 133 | 4-F-phenyl-C(O) | benzyl | CH$_3$C(O) | 3-O(CH$_2$)$_2$morpholin-1-yl | 51% @ 1.0 $\mu$M |
| 134 | phenyl-NH—C(O) | benzyl | CF$_3$C(O) | 3-O(CH$_2$)$_2$morpholin-1-yl | 69% @ 1.0 $\mu$M |
| 135 | (CH$_2$)$_2$NEt$_2$ | (CH$_3$)CH | CCl$_3$C(O) | 3-O(CH$_2$)$_2$N(CH$_3$)$_2$ | 1.6 nM |

TABLE D

| Cpd. | R$_1$ | IC$_{50}$/% Inhibition |
|---|---|---|
| 136 | phenyl-NH—C(O) | 57% @ 1.0 $\mu$M |
| 137 | 4-Br-phenyl-C(O) | 50% @ 1.0 $\mu$M |

Select compounds of the invention were evaluated for their ability to inhibit motilin and erythromycin induced contractions in the rabbit duodenum smooth muscle. Rabbits were fasted 24–48 h and euthanized. The venral midline incision was made approximately 7.5 cm above the umbilicus upto the xyphoid process, exposing the upper peritoneal cavity. The first 8 cm. of the duodenum starting at the pyloric valve was quickly removed and placed in Krebs solution containing NaCl, (120 m), KCl (4.7 mM), $MgSO_4 \cdot 7 H_2O$ (1.2 mM), $CaCl_2 \cdot 2 H_2O$ (2.4 mM), $KH_2PO_4$ (1 mM), D-glucose (10 mM), and $NaHCO_3$ (24 mM). The lumen was flushed with Krebs and excess tissue was removed. The tissue was cut lengthwise, splayed open with the longitudinal muscle layer facing up, and the longitudinal muscle layer was released away from the circular muscle and cut into 3×30 mm strips. A pre-tied 4-0 silk ligature with a loop was placed at the middle of the strip and the strip was folded over the loop so the strip was half its original length. The tissues were mounted in a 10 mL tissue bath (Radnotti Glass Technology, Inc., Monrovia, Calif.) containing Krebs solution gassed with 95% $O_2$ 5% $CO_2$ at 37° C. The tissues were attached to a force displacement transducer (FT03, Grass Instruments, Quincy, Mass.) and resting tension was slowly increased to 1 g. The tissues were allowed to equilibrate for 60–90 min with 2–3 wash cycles. The tissues were equilibrated with two initial contractions induced by a concentration of acetylcholine ($1 \times 10^{-4}$ M) that produced a maximal contraction (0.1 mM), with the highest taken as 100% maximall contraction of that tissue. Base line and response levels are expressed as grams tension developed and as a percent of the response to acetylcholine. The test compounds were dissolved in DMSO (2 mM/100% DMSO) and applied to the prepared strips 5–15 minutes prior to the addition of porcine motilin. After addition, the tension is constantly monitored over 5 min and the maximum tension is recorded. The percent contraction was measured at four ascending concentrations and where appropriate $IC_{50s}$ were determined.

TABLE A

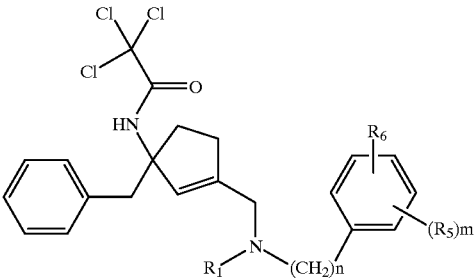

| RWJ/Cpd. | $R_1$ | n | $R_5$ | $R_6$ | $IC_{50}$/% Inhibition |
|---|---|---|---|---|---|
| 8 | phenylNH—C(O) | 0 | 3-O(CH$_2$)$_2$morpholin-1-yl | H | 280 nM** |
| 9 | phenylNH—C(O) | 0 | 3-O(CH$_2$)$_2$morpholin-1-yl | H | 890 nM*** |
| 50 | (CH$_2$)$_2$NEt$_2$ | 0 | 3-OH | H | 98% @ 20 μM |
| 51 | (CH$_2$)$_2$NEt$_2$ | 0 | 3-O(CH$_2$)$_2$NEt$_2$ | H | 74% @ 5 μM |
| 52 | (CH$_2$)$_2$NEt$_2$ | 0 | 3-O(CH$_2$)$_2$piperidin-1-yl | H | 70% @ 10 μM |
| 53 | (CH$_2$)$_2$NEt$_2$ | 0 | 3-O(CH$_2$)$_2$morpholin-1-yl | H | 3.93 mM |
| 54 | (CH$_2$)$_2$NEt$_2$ | 0 | 3-O(CH$_2$)$_3$piperidin-1-yl | H | 24% @ 5 μM |
| 55 | (CH$_2$)$_2$NEt$_2$ | 0 | 3-O(CH$_2$)$_2$pyrrolidin-1-yl | H | 43% @ 2 μM |
| 56 | H | 0 | 4-S(CH$_2$)$_2$NMe$_2$ | H | 24% @ 2 μM |
| 57 | (CH$_2$)$_2$-morpholin-1-yl | 1 | 3-O(CH$_2$)$_2$morpholin-1-yl | H | 1.06 |
| 58 | H | 0 | 4-S(CH$_2$)$_2$NEt$_2$ | H | 44% @ 2.0 μM |
| 10 | phenylC(O) | 0 | 3-O(CH$_2$)$_2$morpholin-1-yl | H | 393 nM |
| 59 | 4-F-phenyl-C(O) | 0 | 3-O(CH$_2$)$_2$morpholin-1-yl | H | 54% @ 3.0 μM |
| 60 | 4-CH$_3$O-phenyl-C(O) | 0 | 3-O(CH$_2$)$_2$morpholin-1-yl | H | 49% @ 10 μM |
| 7 | phenylNH—C(O) | 0 | 3-O(CH$_2$)$_2$morpholin-1-yl | H | 287 nM |
| 61 | 4-Br-phenylC(O) | 0 | 3-O(CH$_2$)$_2$morpholin-1-yl | H | 63% @ 1.0 μM |
| 62 | 3,4-di-F$_2$-phenylC(O) | 0 | 3-O(CH$_2$)$_2$morpholin-1-yl | H | 65% @ 1.0 μM |
| 63 | 3-F-phenyl-NHC(O) | 0 | 3-O(CH$_2$)$_2$morpholin-1-yl | H | 63.8% @ 1.0 μM |

TABLE B

[Structure shown with trichloroacetamide on cyclopentene ring bearing R₂, CH₂-N(R₁)(CH₂)n group, linked to phenyl-O-CH₂CH₂-morpholine]

| Cpd. | R₁ | n | R₂ | IC₅₀/% Inhibition |
|---|---|---|---|---|
| 65 | 4-F-phenyl-C(O) | 0 | 4-MeO-benzyl | 72% @ 1.0 μM |
| 66 | phenyl-C(O) | 0 | 4-MeO-benzyl | 58% @ 1.0 μM |
| 67 | phenyl-NHC(O) | 0 | 4-F-benzyl | 25.7% @ 1.0 μM |
| 68 | phenyl-NHC(O) | 0 | 3-Cl-benzyl | 51% @ 1.0 μM |

Although the claimed compounds are useful as modulators of the motilin receptor, some compounds are more active than others. These compounds are particularly preferred.

The particularly preferred compounds are those where:
$R_1$ is phenylaminocarbonyl, phenylcarbonyl, substituted phenylaminocarbonyl, substituted phenylcarbonyl, and hydrogen;
$R_2$ is phenyl$C_{1-5}$alkyl;
$R_3$ is hydrogen;
$R_4$ is trifluoromethylacetyl;
$R_5$ is O-(CH$_2$)$_2$-morpholin-1-yl;
$R_6$ is hydrogen;
n is 0; and
m is 1.

To prepare the pharmaceutical compositions of this invention, one or more compounds or salts thereof, as the active ingredient, is intimately admixed with a pharmaceutical carrier according to conventional pharmaceutical compounding techniques, which carrier may take a wide variety of forms depending on the form of preparation desired for administration, e.g., oral or parenteral. In preparing the compositions in oral dosage form, any of the usual pharmaceutical media may be employed. Thus for liquid oral preparations, such as for example, suspensions, elixirs and solutions, suitable carriers and additives include water, glycols, oils, alcohols, flavoring agents, preservatives, coloring agents and the like; for solid oral preparations such as, for example, powders, capsules and tablets, suitable carriers and additives include starches, sugars, diluents, granulating agents, lubricants, binders, disintegrating agents and the like. Because of their ease in administration, tablets and capsules represent the most advantageous oral dosage form, in which case solid pharmaceutical carriers are obviously employed. If desired, tablets may be sugar coated or enteric coated by standard techniques. For parenterals, the carrier will usually comprise sterile water, though other ingredients, for example, for purposes such as aiding solubility or for preservation, may be included. Injectable suspensions may also be prepared, in which case appropriate liquid carriers, suspending agents and the like may be employed. The pharmaceutical compositions herein will preferably contain per dosage unit, e.g., tablet, capsule, powder, injection, teaspoonful and the like, from about 5 to about 500 mg of the active ingredient, although other unit dosages may be employed.

In therapeutic use for treating disorders of the gastrointestinal system in mammals, the compounds of this invention may be administered in an amount of from about 0.5 to 100 mg/kg 1-2 times per day orally. In addition the compounds may be administered via injection at 0.1–10 mg/kg per day. Determination of optimum dosages for a particular situation is within the capabilities of formulators.

In order to illustrate the invention, the following examples are included. These examples do not limit the invention. They are meant to illustrate and suggest a method of practicing the invention. Although there are other methods of practicing this invention, those methods are deemed to be within the scope of this invention.

EXAMPLES

Example 1

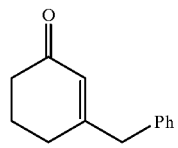

Cpd. 1

A solution of 3-ethoxy-2-cyclohexen-1-one (125 g, 0.89 mol) in ether (500 mL) was added at room temperature to a solution of 2M benzyl magnesium chloride (800 mL) under $N_2$ and stirred for 6 h. The resulting mixture was poured into a solution of 30% $H_2SO_4$ and stirred for 5 h. The resulting organic layer was separated, and the aqueous layer was extracted with several portions of ether. The combined organic layer was dried (MgSO$_4$), and concentrated in vacuo to give compound 1 (161 g) as a colorless oil. NMR (CDCl3): 3.45 (s, 2H, benzylic protons), 5.83 (bs, 1H, olefinic proton), 7.22 (m, 5H, aromatic protons).

Example 2

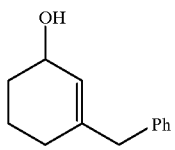
Cpd. 2

A solution of compound 1 (161 g, 0.87 mol) in ether (700 mL) was slowly added to a suspension of LAH (33 g, 0.87 mol) and ether (100 mL) at 0° C. under $N_2$. The resulting mixture was stirred overnight at ambient temperature and cooled to 0° C. Saturated $K_2CO_3$ solution was added to quench the excess LAH, the mixture was filtered through Celite and washed with several portions of ether. The combined organic layers were dried ($MgSO_4$) and concentrated in vacuo to give compound 2 (150 g) as a colorless oil. NMR(CDCl3): 3.23 (s, 2H, benzylic protons), 4.20 (bs, 1H, CHCOH), 5.52 (bs, 1H, olefinic proton), 7.22 (m, 5H, aromatic protons).

Example 3

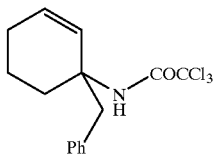
Cpd. 3

A solution of compound 2 (132 g, 0.7 mol) in ether (500 mL) was added to a suspension of hexane washed 60% NaH (27 g, 0.7 mol) in ether (500 mL) at 0° C. under $N_2$ and stirred for 1 h. Trichloroacetonitrile (115 g, 0.8 mol) was slowly added and the resulting mixture was allowed to warm to ambient temperature and stirred overnight. The solvent was removed in vacuo, hexane (1 L) was added and the mixture was cooled to 0° C. Methanol (150 mL) was added and the resulting solid was filtered through Celite. The organic solvent was removed in vacuo to give a crude intermediate (215 g). This intermediate was dissolved in xylene (1 L) and heated to reflux for 3 h under $N_2$. The solvent was removed in vacuo, ether (3 L) and the solid precipitate was filtered to give compound 3 (106 g) as a white crystal: mp 105–06° C.; NMR(CDCl3): 3.20 (Abq, J=8 Hz, 2H), 5.92 (m, 2H, olefinic protons), 6.28 (bs, 1H, NH), 7.22 (m, 5H, aromatic protons).

Example 4

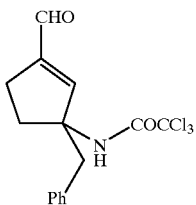
Cpd. 4

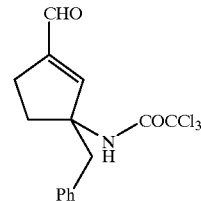
Cpd. 4

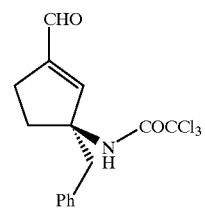
Cpd. 4a

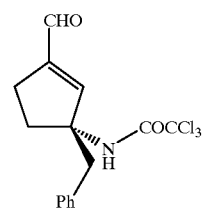
Cpd. 4b

A solution of compound 3 (35 g, mmol) in methylene chloride (500 mL) was treated with ozone at −78° C. until the solution turned blue. The excess of ozone was removed with a stream of $N_2$, dimethyl sulfide (5 mL) was added and the mixture was allowed to warm to room temperature. TsOH-$H_2O$ (3.0 g) was added and the resulting mixture was stirred for 48 h. The solvent was removed in vacuo and residue was dissolved in methylene chloride and treated with hexane. The resulting mixture was stirred for 2 h and the resulting solid was filtered. This solid was washed with hexane and dried in vacuum oven overnight to give compound 4 (21.8 g) as a racemic mixture: mp 162° C. NMR (CDCl3): 3.20 (Abq, J=8 Hz, 2H), 6.85 (bs, 1H, NH), 7.05 (s, 1H, olefinic proton), 7.22 (m, 5H, aromatic protons). 9.91 (s, 1H, CHO). Compound 4 was separated into the pure enantiomers 4a, and 4b by using a chiral column.

Example 5

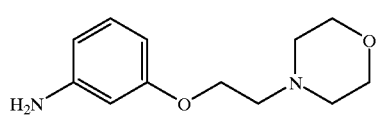
Cpd. 5

A mixture of 3-hydroxyaniline (20.1 g, 190 mmol) $K_2CO_3$ (38 g) and EtOH (300 mL) was stirred at 60° C. for 6 h under $N_2$. The mixture was cooled to room temperature and 2-chloroethylmorpholine (16 g, mmol) was added. The resulting mixture was heated to reflux for 7 h, cooled to room temperature, filtered and the filtrate was concentrated in vacuo. The residue was purified by column chromatography on silica gel using 3 MeOH/ethyl acetate to give compound 5 as a brown oil (22.5 g).

Example 6

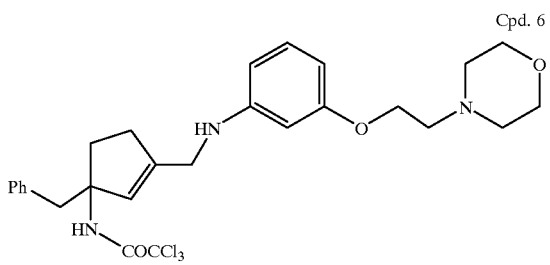

Cpd. 6

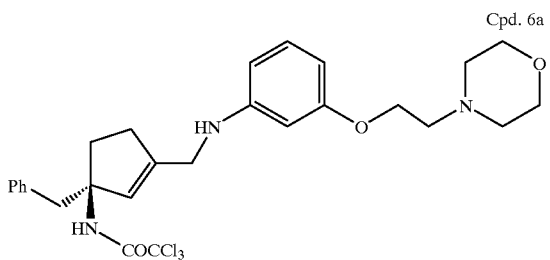

Cpd. 6a

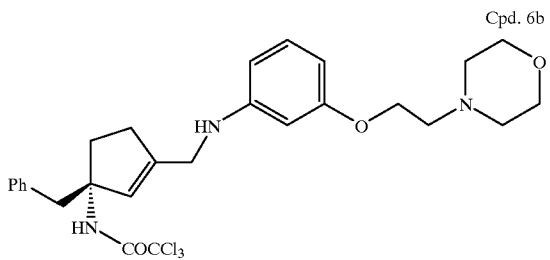

Cpd. 6b

NaCNBH$_4$ (1.0 g) was added in three portions to a solution of compound 4 (7.3 g, 21.0 mmol), compound 5 (6.2 g, 279 mmol) acetic acid (5.5 mL) in methanol (300 mL) at room temperature under N$_2$. and stirred for 30 min. Most of methanol was removed in vacuo and the residue was diluted with methylene chloride, washed with 1N. NaOH and dried. The solvent was removed in vacuo and residue was purified by column chromatography on silica gel using ethyl acetate: hexane 9:1 to give compound 6 (10.3 g) as a light brown oil. NMR(CDCl3): 3.20 (Abq, J=8 Hz, 2H), 5.63 (s, 1H, olefinic proton), 6.61 (bs, 1H, NH). This racemic mixture was separated by HPLC using a chiral column (CHIRALCEL®OD™) and isopropanol and hexane (1:1) as an eluent into 6a and 6b. The oxalate salt of racemic 6, mp 90–92° C. MS (MH$^+$=552)

Example 7
3-Benzyl-3-trichloroacetylamino-1-(N-phenylaminocarbonyl)-N-[(3-(2-morpholinoethoxy)phenyl)amino]methylcyclopentene

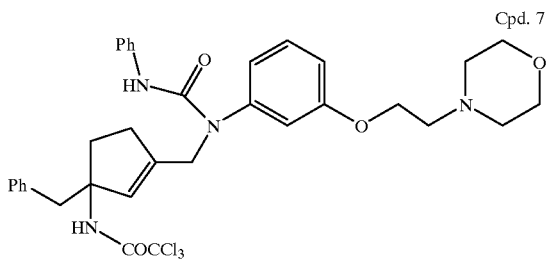

Cpd. 7

To a solution of compound 6 (10.1 g) and triethylamine (0.1 mL) in methylene chloride (300 mL) was added phenyl isocyanate (7.8 g, mmol) at room temperature under N$_2$ dropwise. The resulting mixture was stirred for 24 h and most of solvent was removed in vacuo. The oily residue was purified by column chromatography on silica gel using ethyl acetate hexane 95:5 as an eluent to give an oil (12.5 g). NMR(CDCl3): 3.17 (Abq, J=8 Hz, 2H), 3.73 (m, 4H,CH2NCH2) 4.08 (t, 2H OCH2—) 5.92 (m, 2H, olefinic protons), 6.28 (bs, 1H, NH), 7.22 (m, 5H, aromatic protons). Treatment of the oil with 1N HCl in ether gives compound 7, the title compound (12.2) as a solid: mp. 70–73(dec.) MS 657(MH$^+$)

Example 8
3-Benzyl-3-trichloroacetylamino-1-(N-phenylaminocart)onyl)-N-[(3-(2-morpholinoethoxy)phenyl)amino]methylcyclopentene

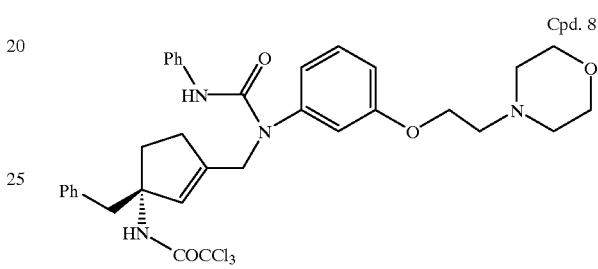

Cpd. 8

To a solution of compound 6b (15 mg) and triethylamine (1 drop) in methylene chloride (5 mL) was added phenyl isocyanate (16 mg) at room temperature under N$_2$ dropwise. The resulting mixture was stirred for 24 h and most of solvent was removed in vacuo. The oily residue was purified by preparative TLC on silica gel using ethyl acetate hexane 95:5 as an eluent to give an oil. Treatment the oil with oxalic acid (or HCl) in ether gives compound 8, the title compound (15 mg) as a solid: mp 92–94° C. MS (MH$^+$=671)

Example 9
3-Benzyl-3-trichloroacetylamino-1-(N-phenylaminocarbonyl)-N-[(3-(2-morpholinoethoxy)phenyl)amino]methylcyclopentene

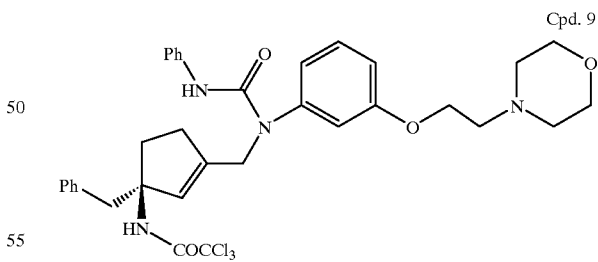

Cpd. 9

To a solution of compound 6a (14 mg) and triethylamine (1 drop) in methylene chloride (5 mL) was added phenyl isocyanate (14 mg) at room temperature under N$_2$ dropwise. The resulting mixture was stirred for 24 h and most of solvent was removed in vacuo. The oily residue was purified by preparative TLC on silica gel using ethyl acetate hexane 95:5 as an eluent to give an oil. Treatment the oil with oxalic acid in ether gives compound 9, the title compound (14 mg) as a solid.

Example 10
3-Benzyl-3-trichloroacetylamino-1-(N-phenylcarbonyl)-N-[(3-(2-morpholinoethoxy)phenyl)amino]methylcyclopentene

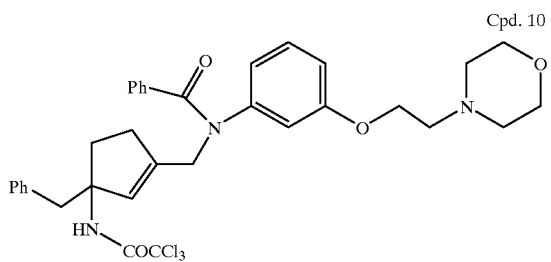

Cpd. 10

Benzoyl chloride (31 mg) was added to a solution of compound 6 (55 mg) and triethylamine (0.3 mL) in methylene chloride (30 mL) at room temperature under $N_2$ and stirred for 2 hours. Most of solvent was removed in vacuo and the oily residue was purified by column chromatography on silica gel using ethyl acetate as an eluent to give a light brown oil (53 mg). This oil was treated with oxalic acid in ether to give the title compound as an off-white powder (47 mg): mp 79–81° C. MS ($MH^+$=656)

Example 11
3-Benzyl-3-trichloroacetylamino-1-(N-phenylaminosulionyl)-N-[(3-(2-morpholinoethoxy)phenyl)amino]methylcyclopentene

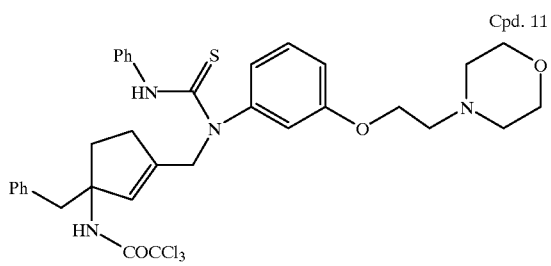

Cpd. 11

Phenyl isothiocyanate (15 mg) was added dropwise to a solution of compound 6 (30 mg) and triethylamine (1 drop) in methylene chloride (5 mL) at room temperature under $N_2$. The resulting mixture was stirred for 24 h and most of solvent was removed in vacuo. The oily residue was purified by prep TLC on silica gel using ethyl acetate hexane 95:5 as an eluent to give an oil. Treatment the oil with 1N HCl in ether gives compound 11, the title compound (33 mg), as a solid: mp 105–108° C. MS ($MH^+$=687)

Example 11

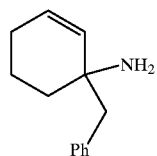

Cpd. 11

A mixture of compound 3 (3.5 g), barium hydroxide (4 g) and EtOH (100 mL) was heated at reflux overnight. The mixture was cooled to room temperature, filtered and concentrated in vacuo. The residue was purified by column chromatography on silica gel using 1% triethylamine/ethyl acetate as an eluent to give compound 11 as a pale yellow oil (1.1 g). NMR; 2.72 (Abq, J=8 Hz, 2H, benzilic protons), 5.54 (bd, J=9 Hz, 1H, olefinic proton at 2 position), 5.63(dt, 1H, the other olefinic proton), 7.23 (m, 5H, aromatic protons).

Example 12

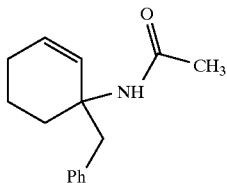

Cpd. 12

A mixture of compound 9 (should be 11) (350 mg) triethylamine (200 mg), acetic anhydride (200 mg) and methylene chloride (50 mL) was stirred at room temperature under $N_2$ for 3 h. The mixture was diluted with methylene chloride (50 mL) and poured into ice cold 1 N NaOH (50 mL). The organic layer was separated, dried and the solvent was removed in vacuo to give compound 12 (376 mg) as a pale yellow oil. NMR(CDCl3): 1.94 (s, 3H, acetyl), 3.10 (Abq, J=8 Hz, 2H), 5.92 (m, 2H, olefinic protons), 6.28 (bs, 1H, NH), 7.22 (m, 5H, aromatic protons).

Example 13

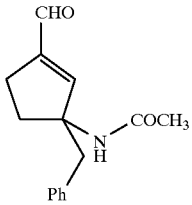

Cpd. 13

A solution of compound 12 (376 mg) in methylene chloride (100 mL) was treated with ozone at −78° C. until the solution turned blue. The excess of ozone was removed with a stream of $N_2$, dimethyl sulfide (0.5 g) was added and the mixture was allowed to warm to room temperature. TsOH-$H_2O$ (100 mg) was added and the resulting mixture was stirred for 4 days. The mixture was poured into ice cold 1N NaOH (50 mL) and the resulting organic layer was separated and purified by column chromatography on silica gel using ethyl acetate and hexane (1:5) as an eluent to give compound 13 (273 mg) as an oil. NMR(CDCl3): 1.96 (s, 3H, acetyl), 3.20 (Abq, J=8 Hz, 2H), 6.85 (bs, 1H, NH), 7.03 (s, 1H, olefinic proton), 7.22 (m, 5H, aromatic protons). 9.85 (s, 1H, CHO).

Example 14

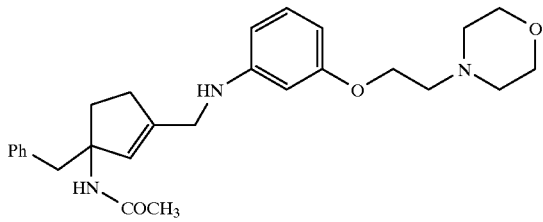

Cpd. 14

NaCNBH$_4$ (150 mg) was added in three portions to a solution of compound 13 (273 mg), compound 5 (297 mg) acetic acid (0.5 mL) in methanol (50 mL) at room temperature under N$_2$. and stirred for 30 min. Most of methanol was removed in vacuo and the residue was diluted with methylene chloride, washed with 1N. NaOH and dried. The solvent was removed in vacuo and residue was purified by column chromatography on silica gel using ethyl acetate-:MeOH:triethylamine (100:1:0.5) to give compound 14 (303 mg) as a light brown oil NMR; 1.88 (s, 3H. acetyl) 3.13 (Abq, J=8 Hz, 2H, benzilic protons), 4.10 (t, J=6 Hz, 2H, phenoxymethylene protons), 5.62 (bs, 1H, olefinic proton),

Example 15
3-Benzyl-3-acetylamino-1-(N-phenylaminocarbonyl)-N-[(3-(2-morpholinoethoxy)phenyl)amino]methylcyclopentene

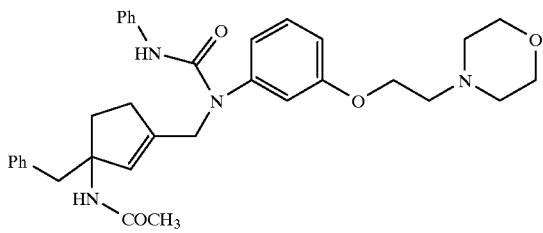

Cpd. 15

To a solution of compound 14 (25 mg) and triethylamine (1 drop) in methylene chloride (5 mL) was added phenyl isocyanate (14 mg) at room temperature under N$_2$. The resulting mixture was stirred for 24 h and most of solvent was removed in vacuo. The oily residue was purified by prep TLC on silica gel using ethyl acetate hexane 95:5 as an eluent to give an oil. Treatment the oil with oxalic acid in ether gives compound 15, the title compound (33 mg) as a solid: mp 85–89° C. MS (MH$^+$=569)

Example 16
Preparation of Compound 16

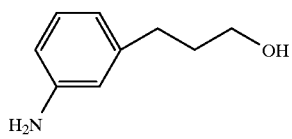

Cpd. 16

A solution 1N BH$_3$/THF (20 mL) was added to a solution of 3-(3-aminophenyl)propionic acid (1.5 g) in THF (15 mL) at 0° C. under N$_2$. After addition the mixture was allowed to warm up to room temperature and was stirred overnight. 2N NaOH was carefully added, the resulting mixture was stirred for 4 h and most of the solvent was removed in vacuo. The residue was extracted with methylene chloride (200 mL) and the organic layer was dried and concentrated in vacuo to give compound 16 as a light yellow oil (1.1 g). NMR (CDCl3);3.71 (t, J=6 Hz, 2H, CH2OH), 6.72~7.13 (m, 4H, aromatic protons).

Example 17
Preparation of Compound 17

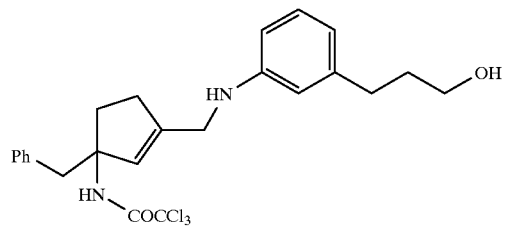

Cpd. 17

NaCNBH$_4$ (30 mg) was added in three portions to a solution of compound 4 (150 mg), compound 16 (100 mg) and acetic acid (10 drops) in methanol (25 mL) at room temperature under N$_2$. and stirred for 30 min. Most of methanol was removed in vacuo and the residue was diluted with methylene chloride, washed with 1N. NaOH and dried. The solvent was removed in vacuo and residue was purified by column chromatography on silica gel using ethyl acetate-:hexane (1:1) to give compound 15 (201 mg) as a pale yellow oil. NMR(CDCl3); 3.16 (Abq, J=8 Hz, 2H, benzilic protons), 3.72 (t. J=6 Hz, 2H, CH2OH), 3.82 (s, 2H, CH2N), 5.62 (s, 1H, olefinic proton), 6.50~7.25 (m, 9H, aromatic protons).

Example 18

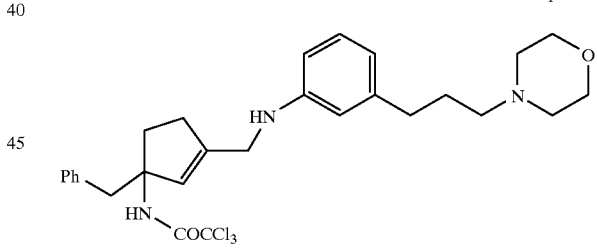

Cpd. 18

Mesyl chloride (46 mg) was added to a solution of compound 17 (2.01 mg) and triethylamine (0.2 mL)in methylene chloride (50 mL) at -5° C. under N$_2$. This mixture was stirred for 5 min and MeOH (2 drops) was added and the resulting mixture was allowed to warm to room temperature and poured into 1N NaOH (10 mL). The organic layer was separated, dried and the solvent was removed in vacuo to give a thick brown oil. This oil was dissolved in THF (10 mL) and morpholine (50 mg) and the resulting mixture was heated at reflux for 16 h. The mixture was cooled to room temperature and the solvent was removed in vacuo. The residue was purified by column chromatography on silica gel using ethyl acetate:triethylamine (100:0.5) to give compound 18 (85 mg) as a pale yellow oil. NMR(CDCl3); 3.18 (Abq, J=8 Hz, 2H, benzilic protons), 3.82 (s, 2H, CH2N), 5.62 (s, 1H, olefinic proton), 6.50~7.25 (m, 9H, aromatic protons).

Example 19

3-Benzyl-3-trichloroacetylamino-1-(N-phenylaminocart)onyl)-N-[(3-(3-morpholinopropyl)phenyl)amino]methylcyclopentene

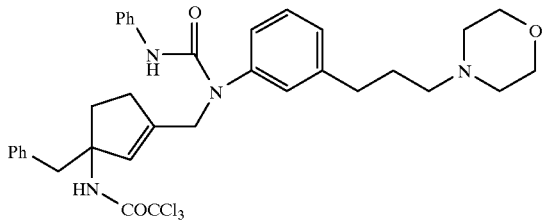
Cpd. 19

To a solution of compound 18 (32 mg) and triethylamine (1 drop) in methylene chloride (5 mL) was added phenyl isocyanate (25 mg) at room temperature under $N_2$ dropwise. The resulting mixture was stirred for 24 h and most of solvent was removed in vacuo. The oily residue was purified by preparative TLC on silica gel using ethyl acetate hexane 95:5 as an eluent to give an oil (41 mg). Treatment of the oil with oxalic acid in ether gives compound 19, the title compound (40 mg) as a solid: mp 85–88° C. MS (MH$^+$=669)

Example 20

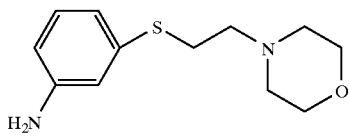
Cpd. 20

A mixture of 3-aminothiophenol (1.25 g, 10.0 mmol), 2-chloroethylmorpholine (2.3 g, 12.0 mmol) and $K_2CO_3$ (1.8 g) in THF (150 mL) was heated to reflux for 8 h. The resulting mixture was filtered and partitioned between $H_2O$ and ethyl actetate. The aqueous layer was washed with several portions of ethyl actetate and the combined organic extracts were dried $Na_2SO_4$ and concentrated in vacuo. The residue was purified by column chromatography on silica gel using 10% MeOH/ethyl acetate as an eluent to give compound 20 as an oil (600 mg). NMR(CDCl3); 2.60 (t, J=6 Hz, 2H, CH2N), 3.02 (t, J=6 Hz, 2H, CH2S), 6.44~7.06 (m, 4H, aromatic protons).

Example 21

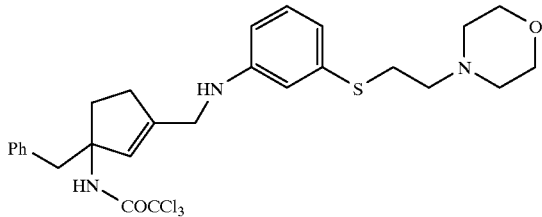
Cpd. 21

NaCNBH$_4$ (300 mg) was added in three portions to a solution of compound 4 (800 mg), compound 20 (600 mg), and acetic acid (2.0 mL) in methanol (100 mL) at room temperature under $N_2$. The reaction mixture was stirred for 30 min, most of methanol was removed in vacuo. The residue was diluted with methylene chloride, washed with 1N. NaOH and dried. The solvent was removed in vacuo and residue was purified by column chromatography on silica gel using ethyl acetate: MeOH:triethylamine (100:2:0.1) to give compound 21 (735 mg) as a pale yellow oil. NMR (CDCl3); 3.18 (Abq, J=8 Hz, 2H, benzilic protons), 3.82 (s, 2H, CH2N), 5.62 (s, 1H, olefinic proton), 6.50~7.25 (m, 9H, aromatic protons). MS (MH$^+$=568)

Example 22

3-Benzyl-3-trichloroacetylamino-1-(N-phenylaminocarbonyl)-N-[(3-(2-morpholinoethyl)phenyl)thio]methylcyclopentene

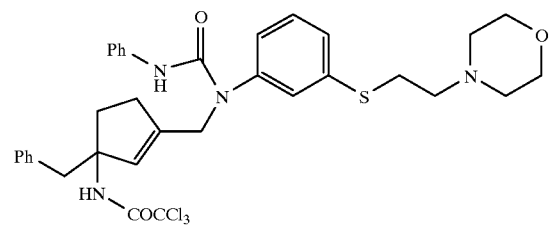
Cpd. 22

To a solution of compound 18 (53 mg) and triethylamine (1 drop) in methylene chloride (30 mL) was added phenyl isocyanate (38 mg) at room temperature under $N_2$ dropwise. The resulting mixture was stirred for 24 h and most of solvent was removed in vacuo. The oily residue was purified by column chromatography on silica gel using ethyl acetate:triethylylamine (100:0.2) as an eluent to give an oil (55 mg). Treatment the oil with oxalic acid in ether gives compound 19, the title compound (57 mg) as a white solid: mp 88–92° C. MS (MH$^+$=687)

Example 23

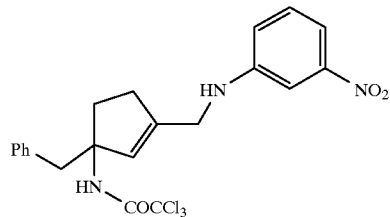
Cpd. 23

NaCNBH$_4$ (589 mg) was added in three portions to a solution of compound 4 (2.0 g), 3-nitroaniline (1.59 g, 11.5 mmol) acetic acid (2 mL) in methanol (100 mL) at room temperature under $N_2$. and stirred overnight. Most of methanol was removed in vacuo and the residue was diluted with methylene chloride, washed with 1N. NaOH and dried. The solvent was removed in vacuo and residue was purified by column chromatography on silica gel using ethyl acetate-:hexane 1:1 to give compound 23 (2.0 g) as a pale yellow oil. NMR(CDCl3); 3.18 (Abq, J=8 Hz, 2H, benzylic protons), 3.85 (d, J=6 Hz, 2H, CH2N), 5.62 (s, 1H, olefinic proton), 6.80~7.44 (m, 9H, aromatic protons).

Example 24

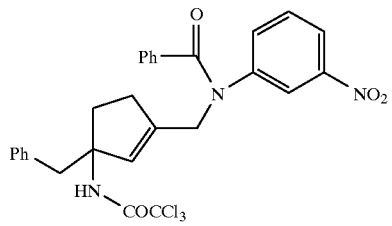
Cpd. 24

Benzoyl chloride (125 mg, 0.89 mmol) was added to a solution of compound 23 (350 mg, 0.748 mmol) and triethylamine (1.3 mg) in methylene chloride (30 mL) at room temperature under $N_2$ and this mixture was stirred for 2 h. Most of solvent was removed in vacuo and the oily residue was purified by column chromatography on silica gel using ethyl acetate:hexane (1:4) as an eluent to give compound 24 as a light brown oil (350 mg). NMR(CDCl3); 3.18 (Abq, J=8 Hz, 2H, benzylic protons), 4.65 (d, J=8 Hz, 2H, CH2N), 5.62 (s, 1H, olefinic proton), 6.08~8.01 (m, 14H, aromatic protons).

Example 25

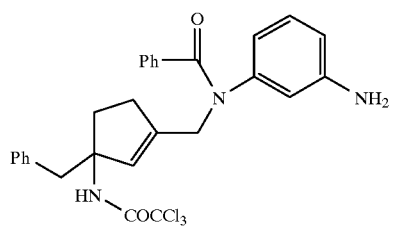
Cpd. 25

A mixture of compound 24 (350 mg, 0.61 mmol), 10% Pd/C (5 mg) and acetic acid (2 drops) in EtOH (20 mL) was hydrogenated at 50 psi at room temperature for 8 h. The resulting mixture was filtered through Celite and concentrated in vacuo. The residue was treated with methylene chloride (300 mL) washed with $H_2O$, dried and the solvent was removed in vacuo. The residue was purified by column chromatography on silica gel using ethyl acetate as an eluent to give compound 25 (200 mg) as an oil. NMR(CDCl3); 3.18 (Abq, J=8 Hz, 2H, benzylic protons), 4.58 (d, J=8 Hz, 2H, CH2N), 5.62 (s, 1H, olefinic proton), 6.28–7.41 (m, 14H, aromatic protons).

Example 26

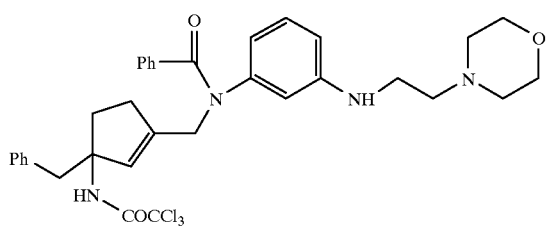
Cpd. 23a

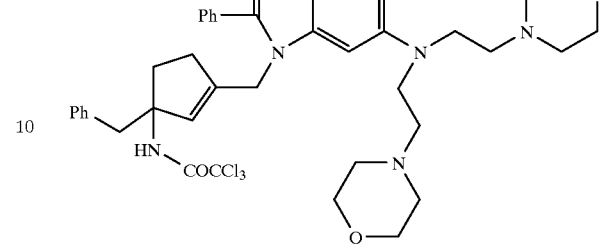
Cpd. 23b

A solution of compound 25 (160 mg, 0.3 mmol), chloroethylmorpholine (82 mg, 0.44 mmol), and DBU (101 mg) in 2-propanol (25 mL) was heated to reflux for 2 days. The solvent was removed in vacuo and the residue was treated with 0.5 N NaOH (100 mL) and extracted with several portions of ethyl acetate. The organic layer was dried concentrated in vacuo. The residue was purified by column chromatography on silica gel. The bis-alkylated compound (84 mg) was eluted with ethyl acetate:MeOH 95:5. This compound was treated with oxalic acid and ether to give compound 23a (70 mg) as a solid. mp 86–92° C. MS ($MH^+$=655)

Continued elution with methylene chloride:MeOH:triethylamine 85:10:5) to give the mono-alkylated product 23b, which was converted to the oxalate salt with oxalic acid and ether (40 mg). mp 88–96° C. MS ($MH^+$=768)

Example 27

Cpd. 27

NaCNBH$_4$ (146 mg) was added in three portions to a solution of 4-chlorobenzaldehyde (308 mg, 2.2 mmol), 3-aminophenol (200 mg, 1.83 mmol) acetic acid (1.0 mL) in methanol (100 mL) at room temperature under $N_2$. and stirred for 30 min. Most of methanol was removed in vacuo and the residue was diluted with methylene chloride, washed with 1N. NaOH and dried. The solvent was removed in vacuo and residue was purified by column chromatography on silica gel using ethyl acetate to give compound 27 (230 mg) as a pale yellow oil. NMR(CDCl3); 4.26 (s, 2H, benzylic protons), 6.10~7.24 (m, 8H, aromatic protons). MS ($MH^+$=234)

Compound 28

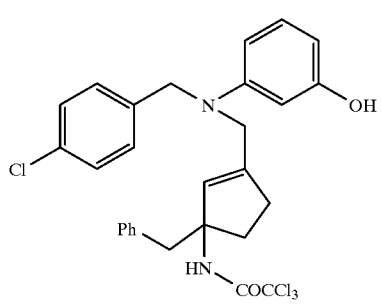
Cpd. 28

NaCNBH$_4$ (60 mg) was added in three portions to a solution of compound 4 (259 mg), compound 27 (230 mg,) and acetic acid (1.0 mL) in methanol (50 mL) at room temperature under N$_2$. and stirred for 16 h. Most of methanol was removed in vacuo and the residue was diluted with methylene chloride, washed with 1N. NaOH and dried. The solvent was removed in vacuo and residue was purified by column chromatography on silica gel to give compound 28 (100 mg) as an oil. NMR(CDCl3); 3.18 (Abq, J=8 Hz, 2H, benzylic protons), 4.00 (d, J=8 Hz, 2H, CH2N), 4.42(s, 2H, 4-chlorobenzyl protons), 5.42 (s, 1H, olefinic proton), 6.21~7.25 (m, 13H, aromatic protons).

Example 29

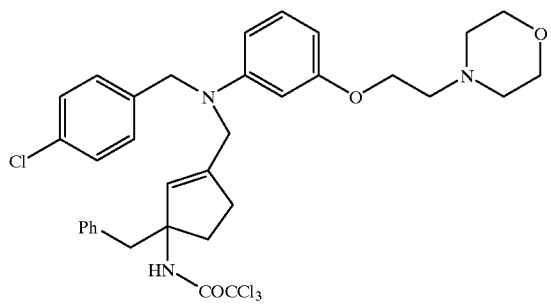
Cpd. 29

A solution of compound 28 (100 mg, 0.18 mmol), chloroethylmorpholine (100 mg, 0.6 mmol), and DBU (115 mg) in 2-propanol (50 mL) was heated to reflux for 2 days. The solvent was removed in vacuo and the residue was treated with 0.5 N NaOH (100 mL) and extracted with several portions of ethyl acetate. The organic layer was dried concentrated in vacuo. The residue was purified by column chromatography on silica gel using ethyl acetate:hexane (1:1) to give an oil (95 mg). Treatment of the oil with oxalic acid and ether gives compound 29, the title compound as a solid:mp 134–136. MS (MH$^+$=676)

Example 30

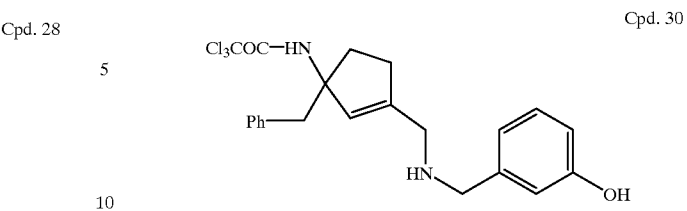
Cpd. 30

NaCNBH$_4$ (35.3 mg) was added in three portions to a solution of compound 4 (150 mg, 0.43 mmol), 3-hydroxybenzylamine (104.8 mg, 0.87 mmol) acetic acid (1.0 mL) in methanol (50 mL) at room temperature under N$_2$. and stirred for 16 h. Most of methanol was removed in vacuo and the residue was diluted with methylene chloride, washed with 1N. NaOH and dried. The solvent was removed in vacuo and residue was purified by column chromatography on silica gel to give compound 30 (160 mg) as an oil. NMR(CDCl3); 3.18 (Abq, J=8 Hz, 2H, benzylic protons), 3.38 (s,2H, 3-hydroxybenzyl protons), 3.72 (d, J=8 Hz, 2H, CH2N), 5.62 (s, 1H, olefinic proton), 6.68~7.25 (m, 9H, aromatic protons).

Example 31

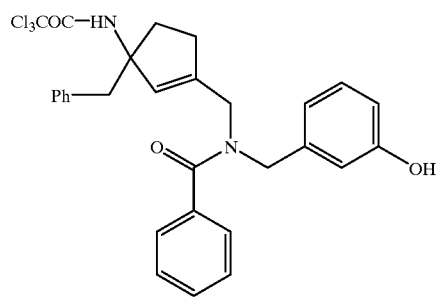
Cpd. 31

Benzoyl chloride (69 mg, 0.5 mmol) was added to a solution of compound 30 (150 mg, 0.33 mmol) and triethylamine (1.0 mL) in methylene chloride (20 mL) at room temperature under N$_2$ and stirred for 16 h. Most of solvent was removed in vacuo and the oily residue was purified by column chromatography on silica gel using ethyl acetate:hexane 1:4 as an eluent to give compound 31 as a light brown oil (220 mg). NMR(CDCl3); 3.18 (Abq, J=8 Hz, 2H, benzylic protons), 5.59 and 5.62, (both s, 1H total, olefinic proton, two rotamer?), 6.60~8.15 (m, 14H, aromatic protons).

Example 32

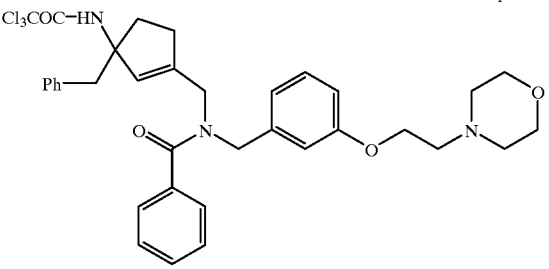
Cpd. 32

A solution of compound 31 (220 mg, 0.4 mmol), chloroethylmorpholine (280 mg, 1.4 mmol), and DBU (120 mg) in 2-propanol (100 mL) was heated to reflux for 16 h. The solvent was removed in vacuo and the residue was treated with 0.5 N NaOH (100 mL) and extracted with several portions of ethyl acetate. The organic layer was dried concentrated in vacuo. The residue was purified by column chromatography on silica gel using ethyl acetate:MeOH (9:1) to give an oil (95 mg). Treatment of the oil with oxalic acid and ether gives compound 32, the title compound as a solid:mp 90–95. MS (MH$^+$=670)

Example 33

Cpd. 33

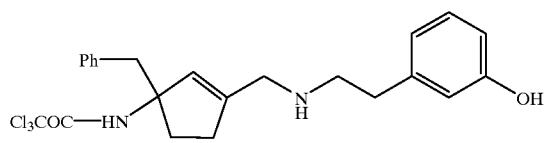

Benzoyl chloride (280 mg) was added to a solution of compound 24 (300 mg) and triethylamine (2.0 mL) in methylene chloride (30 mL) at room temperature under N$_2$ and stirred for 2 hours. Most of solvent was removed in vacuo and the oily residue was purified by column chromatography on silica gel using ethyl acetate:hexane 1:4 as an eluent to give compound 33 as a light brown oil (265 mg). NMR(CDCl3); 3.18 (Abq, J=8 Hz, 2H, benzylic protons), 3.35 (s, 2H, allylic methylene protons) 5.61 (s, 1H, olefinic proton) 6.60~7.23 (m, 9H, aromatic protons). MS (MH$^+$=467)

Example 34 (two-step procedure)

Cpd. 34

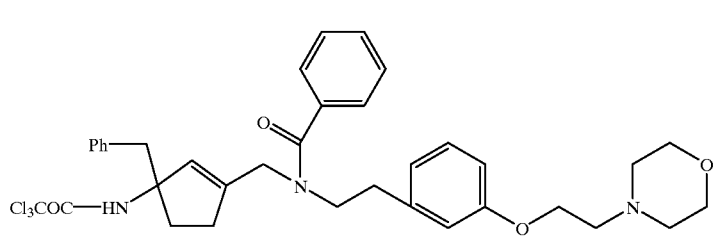

A solution of compound 33 (265 mg, 0.46 mmol), chloroethylmorpholine (173 mg, 0.8 mmol), and DBU (107 mg) in 2-propanol (50 mL) was heated to reflux for 16 h. The solvent was removed in vacuo and the residue was treated with 0.5 N NaOH (100 mL) and extracted with several portions of ethyl acetate. The organic layer was dried concentrated in vacuo. The residue was purified by column chromatography on silica gel using ethyl acetate:MeOH (95:5) to give an oil (165 mg). Treatment of the oil with oxalic acid and ether gives compound 34, the title compound as a solid:mp 126–28° C. MS (MH$^+$=684)

Example 35

Compound 35

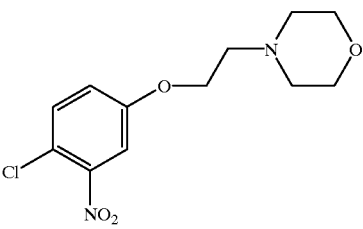

A solution of 4-chloro-3-nitrophenol (2.0 g, 11.53 mmol), chloroethylmorpholine (2.57 g, 13.8 mmol), and K$_2$CO$_3$ (5.0 g) in 2-propanol (200 mL) was heated to reflux for 16 h. The solvent was removed in vacuo and the residue was treated with 0.5 N NaOH (100 mL) and extracted with several portions of ethyl acetate. The organic layer was dried and concentrated in vacuo to give compound 35 as an oil. NMR(CDCl3); 4.18 (t, J=6 Hz, 2H, phenoxymethylene protons), 7.09~7.44 (m, 3H, amomatic protons).

Example 36

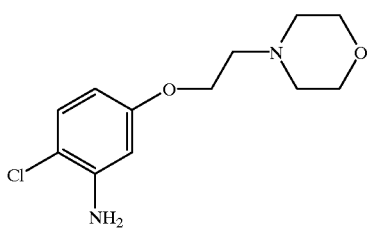

A mixture of compound 35 (500 mg, 1.84 mmol), 10% Pd/C (5 mg) and acetic acid (2 drops) in EtOH (20 mL) was hydrogenated at 55 psi at room temperature for 16 h. The resulting mixture was filtered through Celite and concentrated in vacuo. The residue was treated with methylene chloride (300 mL) washed with H$_2$O, dried and the solvent was removed in vacuo. The residue was purified by column chromatography on silica gel using ethyl acetate:MeOH (95:5) as an eluent to give compound 36 (200 mg) as an oil. NMR(CDCl3); 4.06 (t, J=6 Hz, 2H, phenoxymethylene protons), 6.35~7.10 (m, 3H, aromatic protons).

Example 37

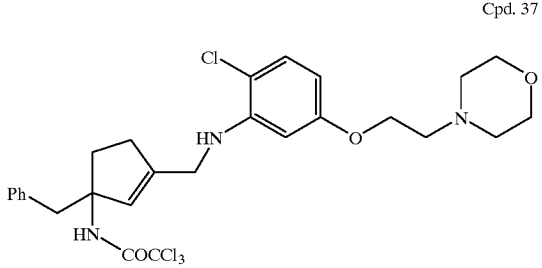

Cpd. 37

NaCNBH$_4$ (53 mg) was added in three portions at room temperature under N$_2$ to a solution of compound 4 (243 mg, 0.7 mmol), compound 36 (200 mg, 0.78 mmol), and acetic acid (2.0 mL) in methanol (75 mL). This mixture was stirred for 16 h and most of methanol was removed in vacuo The residue was diluted with methylene chloride, washed with 1N. NaOH and dried. The solvent was removed in vacuo and residue was purified by column chromatography on silica gel using ethyl acetate:MeOH (95:5) as an eluent to give compound 37 (250 mg) as an oil. NMR(CDCl3); 3.18 (Abq, J=8 Hz, 2H, benzylic protons), 4.08 (t, J=6 Hz, 2H, phenoxymethylene protons), 5.62 (s, 1H, olefinic proton), 6.22~7.30 (m, 8H, aromatic protons).

Example 38

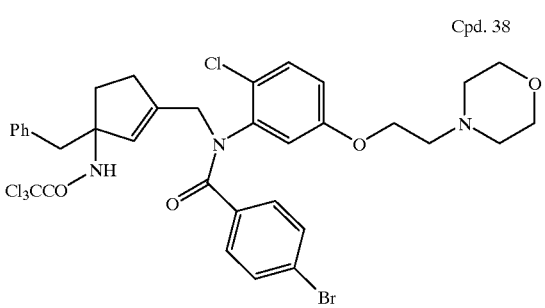

Cpd. 38

4-Bromobenzoyl chloride (25 mg) was added to a solution of compound 37 (45 mg) and triethylamine (1.0 mL) in methylene chloride (25 mL) at room temperature under N$_2$. The reaction mixture was stirred for 16 h and most of solvent was removed in vacuo. The oily residue was purified by preparative TLC using ethyl acetate as an eluent to give an oil (25 mg). Treatment of the oil with oxalic acid in ether gives compound 38 (20 mg). MS (MH$^+$=768)

Example 39

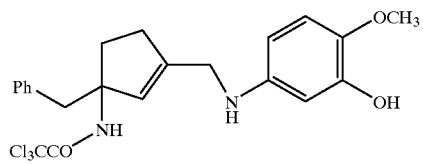

Cpd. 39

NaCNBH$_4$ (204 mg) was added in three portions to a solution of compound 4 (1.04 g, 3.0 mmol), 3-hydroxy-4-methoxyaniline (835 mg, 6.1 mmol), and acetic acid (2.0 mL) in methanol (100 mL) at room temperature under N$_2$. The reaction mixture was stirred for 6 h and most of methanol was removed in vacuo. The residue was diluted with methylene chloride, washed with 1N. NaOH and dried. The solvent was removed in vacuo and residue was purified by column chromatography on silica gel using ethyl acetate-:hexane (1:1) as an eluent to give compound 39 (1.2 g) as an oil. NMR(CDCl3); 3.18 (Abq, J=8 Hz, 2H, benzylic protons), 4.79 (s, 3H, CH3O), 5.62 (s, 1H, olefinic proton), 6.12~7.32 (m, 8H, aromatic protons).

Example 40

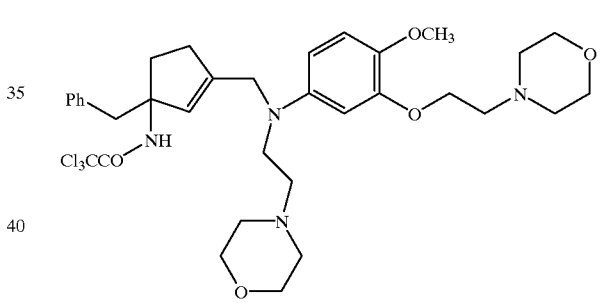

Cpd. 40

A solution of compound 39 (500 mg, 1.06 mmol), chloro-ethylrriorpholine (394 mg, 2.12 mmol), and DBU (490 mg) in 2-propanol (100 mL) was heated to reflux for 16 h. The solvent was removed in vacuo and the residue was treated with 0.5 N NaOH (100 mL) and extracted with several portions of ethyl acetate. The organic layer was dried concentrated in vacuo. The residue was purified by column chromatography on silica gel using ethyl acetate:MeOH:triethylamine (85:10:5) to give an oil. Treatment of the oil with oxalic acid and ether gives compound 40, the title compound as a solid:mp 92–95° C. MS (MH$^+$=695)

Example 41

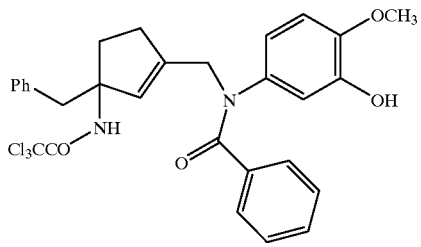
Cpd. 41

Benzoyl chloride (43 mg, 0.3 mmol) was added to a solution of compound 40 (120 mg, 0.26 mmol) and triethylamine (1.0 mL) in methylene chloride (50 mL) at room temperature under $N_2$. The mixture was stirred for 6 h, poured into 1N NaOH and extracted with methylene chloride. The organic extracts were combined, dried, and concentrated in vacuo. The oily residue was purified by column chromatography on silica gel using ethyl acetate:hexane (1:1) as an eluent to give compound 41 an oil (100 mg). NMR(CDCl3); 3.18 (Abq, J=8 Hz, 2H, benzylic protons), 3.81(S, 3H, CH3O), 4.60 (d, J=8 Hz, 2H, CH2N), 5.62 (s, 1H, olefinic proton), 6.60~7.38 (m, 13H, aromatic protons).

Example 42

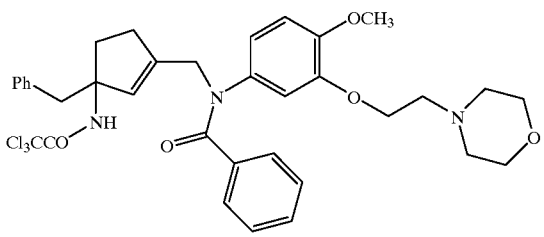
Cpd. 41

A solution of compound 41 (100 mg, 0.17 mmol), chloro-ethylmorpholine (64.7 mg, 0.35 mmol), and DBU (300 mg) in 2-propanol (50 mL) was heated to reflux for 16 h. The solvent was removed in vacuo and the residue was treated with 0.5 N NaOH (100 mL) and extracted with several portions of ethyl acetate. The organic layer was dried concentrated in vacuo. The residue was purified is by column chromatography on silica gel using ethyl acetate-:MeOH (9:1) to give an oil. Treatment of the oil with oxalic acid and ether gives compound 42 (81 mg), the title compound as a solid:mp 85–91° C. MS (MH+=686)

Example 42

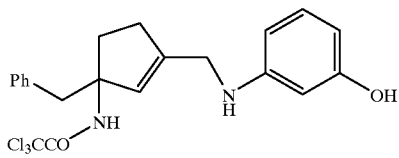
Cpd. 42

NaCNBH4 (250 mg) was added in three portions to a solution of compound 4 (510 mg, 1.6 mmol), 3-aminophenol (515 mg, 4.9 mmol) acetic acid (1.0 mL) in methanol (200 mL) at room temperature under $N_2$. The reaction mixture was stirred for 30 min and most of the methanol was removed in vacuo. The residue was diluted with methylene chloride, washed with 1N. NaOH, dried and concentrated in vacuo. The residue was purified by column chromatography on silica gel using ethyl acetate:hexane (1:2) as an eluent to give compound 42 (385 mg) as a pale yellow oil. NMR (CDCl3); 3.18 (Abq, J=8 Hz, 2H, benzylic protons), 3.80 (ABq, J=8 Hz, 2H, CH2N), 5.62 (s, 1H, olefinic proton), 6.21~7.25 (m, 9H, aromatic protons).

Example 43

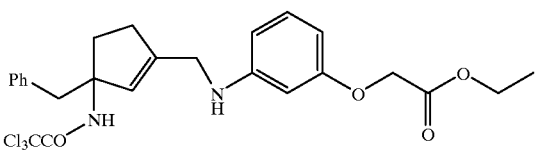
Cpd. 43

A mixture of compound 42 (251 mg), $K_2CO_3$ (1.1 g) ethylbromoacetate (200 mg) THF (70 mL) was heated to 50° C. for 8 h. The resulting mixture was filtered through Celite and concentrated in vacuo. The residue was purified by column chromatography on silica gel using ethyl acetate-:hexane (1:3) to give compound 43 a as a pale yellow oil (263 mg). Treatment of the oil with concentrated HCl and MeOH gives compound 43 as a white foam (89 mg): mp 64–66° C. MS (MH+=525)

Example 45

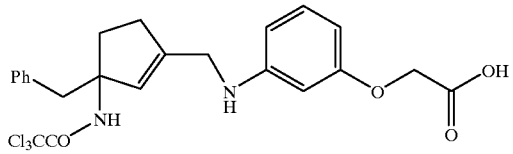
Cpd. 45

A solution of compound 43a (59 mg), 1N NaOH (1mL) in MeOH (5 mL) was stirred at room temperature under $N_2$. for 3 h. Most of the MeOH was removed in vacuo and the residue was diluted with $H_2O$ (10 mL). This mixture was acidified to pH 4 using 0.1N HCl and extracted with methylene chloride. The combined organic extracts were dried and concentrated in vacuo to give compound 45, the title compound as a light brown powder (35 mg): mp 70–73° C. MS (MH+=497)

Example 46

Cpd. 46

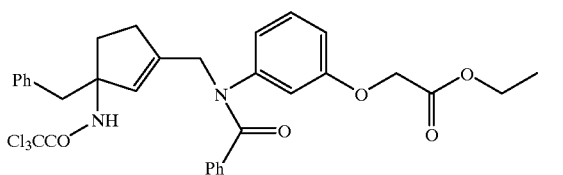

Benzoyl chloride (31 mg) was added to a solution of compound 43a (45 mg) and triethylamine (0.1 mL) in methylene chloride (30 mL) at room temperature under $N_2$ and stirred for 5 h. The resulting mixture was poured into 1N NaOH and extracted with methylene chloride. The combined organic extracts were combined, dried and concentrated in vacuo. Most of solvent was removed in vacuo and the oily residue was purified by using ethyl acetate:hexane (3:5) as an eluent to give compound 46 as a pale yellow oil (100 mg). MS ($MH^+$=629)

What is claimed is:
1. A compound of the Formula I:

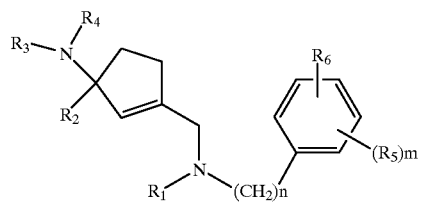

I wherein
$R_1$ is selected from hydrogen, $C_{1-5}$alkyl, substituted $C_{1-5}$alkyl (where the alkyl substituents are one or more halogens), amino$C_{1-5}$alkyl, $C_{1-5}$alkylamino$C_{1-5}$alkyl, di-$C_{1-5}$alkylamino$C_{1-5}$alkyl, $R_aR_bN$-$C_{1-5}$alkyl (where the $R_a$ and $R_b$ are independently selected from hydrogen and $C_{1-5}$alkyl, or are taken together to form a morpholine, piperazine, piperidine, or N-substituted piperidine where the N-substitutent is $C_{1-5}$alkyl or phenyl$C_{1-5}$alkyl), $C_{1-5}$alkylcarbonyl, $C_{1-5}$alkoxycarbonyl, aminocarbonyl, $C_{1-9}$alkylaminocarbonyl, cyclo$C_{3-9}$alkylaminocarbonyl, pyridinylcarbonyl, substituted pyridinylcarbonyl (where the pyridinyl substituents are selected from the group consisting of one or more halogens and $C_{1-5}$alky), thiophenecarbonyl, substituted thiophenecarbonyl (where the thiophene substituents are selected from the group consisting of one or more halogens and $C_{1-5}$alkyl), phenyl, phenyl$C_{1-5}$alkyl, phenoxycarbonyl, phenylcarbonyl, diphenylmethylcarbonyl, phenylaminocarbonyl, phenylthiocarbonyl, phenylaminothiocarbonyl, substituted phenyl, substituted phenyl$C_{1-5}$alkyl, substituted phenoxycarbonyl, substituted phenylcarbonyl, substituted phenylaminocarbonyl, substituted diphenylmethylcarbonyl, substituted phenylthiocarbonyl, and substituted phenylaminothiocarbonyl (where the phenyl substituents are selected from the group consisting of one or more of halogen, $C_{1-5}$alkyl, trihalomethyl, $C_{1-5}$alkoxy, amino, nitrile, nitro, $C_{1-5}$alkylamino, di-$C_{1-5}$alkylamino, if there are more than one substitutents they may be taken together with the phenyl ring to form a fused bicyclic 7–10 membered heterocyclic ring having one to two heteroatoms selected from oxygen, sulfur or nitrogen or the substituents may be taken together to form a fused bicyclic 7–10 membered aromatic ring;

$R_2$ is selected from hydrogen, $C_{1-5}$alkyl, $C_{1-5}$alkoxy, phenyl, substituted phenyl (where the phenyl substituents are selected from one or more of the group consisting of halogen and $C_{1-5}$alkyl), phenyl$C_{1-5}$alkyl, substituted phenyl$C_{1-5}$alkyl (where the phenyl substituents are selected from one or more of the group consisting of halogen, $C_{1-5}$alkyl, $C_{1-5}$alkoxy, halo and di-$C_{1-5}$alkylamino)

$R_3$ is selected from hydrogen, $C_{1-5}$alkylcarbonyl, substituted $C_{1-5}$alkylcarbonyl (where the alkyl substituents are selected from one or more halogens), phenylcarbonyl, and substituted phenylcarbonyl (where the phenyl substituents are selected from one or more of the group consisting of halogen, $C_{1-5}$alkyl, $C_{1-5}$alkoxy, amino, $C_{1-5}$alkylamino, and di-$C_{1-5}$alkylamino)

$R_4$ is selected from hydrogen, $C_{1-5}$alkylcarbonyl, substituted $C_{1-5}$alkylcarbonyl (where the alkyl substituents are selected from one or more halogens), phenylcarbonyl, and substituted phenylcarbonyl (where the phenyl substituents are selected from one or more of the group consisting of halogen, $C_{1-5}$alkyl, $C_{1-5}$alkoxy, amino, $C_{1-5}$alkylamino, and di-$C_{1-5}$alkylamino)

n is 0–3;
m is 1–5
$R_5$ is

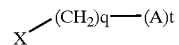

where:
q is 0–2;
t is 0–1;
X is oxygen, $CH_2$, sulfur, or $NR_c$ where
$R_3$ is hydrogen, $C_{1-5}$alkyl, morpholino$C_{1-5}$alkyl, piperidinyl$C_{1-5}$alkyl, N-phenylmethylpiperidinyl or piperazinyl$C_{1-5}$alkyl, with the proviso that if q and t are 0, then X is hydroxy, thiol, or amino,
A is $C_{1-5}$alkoxycarbonyl, phenylcarbonyl, or $R_7R_8N$—
where $R_7$ is independently selected from hydrogen, $C_{1-5}$alkyl, cyclo$C_{1-9}$alkyl, or $R_7$ is taken together with $R_8$ to form a 5 or 6 membered heterocyclic ring with one or more heteroatoms selected from the group consisting of oxygen, nitrogen or sulfur and N-oxides thereof;
$R_8$ is independently selected from hydrogen, $C_{1-5}$alkyl, cyclo$C_{1-9}$alkyl or taken together with $R_7$ to form a 5 or 6 membered heterocyclic ring with one or more heteroatoms selected from the group consisting of oxygen, nitrogen or sulfur, and N-oxides thereof;
$R_6$ is selected from hydrogen, halogen, $C_{1-5}$alkoxy, $C_{1-5}$alkylamino, or di-$C_{1-5}$alkylamino;
and the pharmaceutically acceptable salts thereof.
2. The compound of claim 1 wherein:
$R_6$ is selected from phenylaminocarbonyl, phenylcarbonyl, substituted phenylaminocarbonyl, substituted phenylcarbonyl, and hydrogen;
$R_2$ is phenyl$C_{1-5}$alkyl;

R₃ is hydrogen;
R₄ is trifluoromethylacetyl;
R₅ is O-(CH₂)₂-morpholin-1-yl;
R₆ is hydrogen
n is 0; and
m is 1.

3. The compound according to claim 1 of the formula:

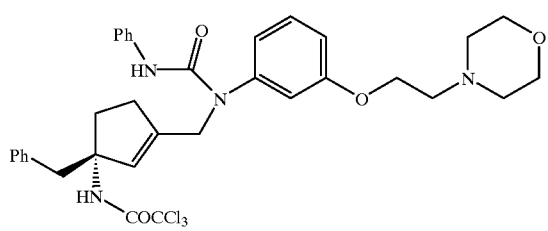

4. The compound according to claim 1 of the formula:

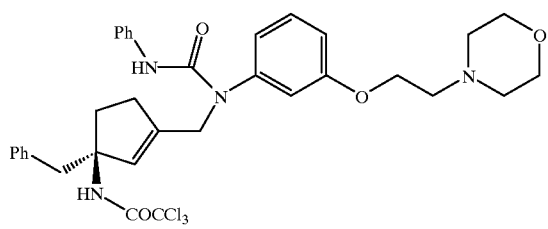

5. The compound according to claim 1 of the formula:

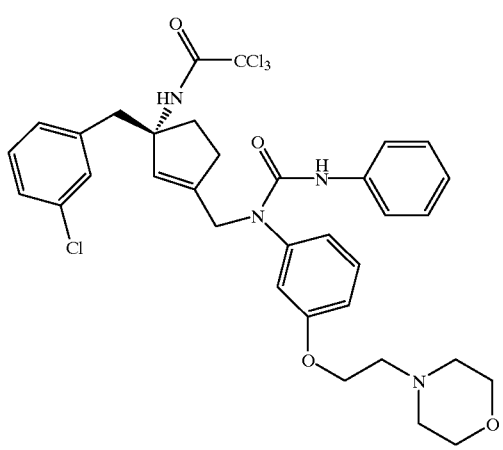

6. The compound according to claim 1 of the formula:

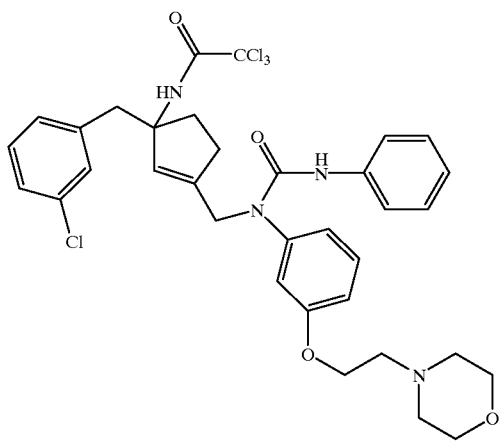

7. The compound according to claim 1 of the formula:

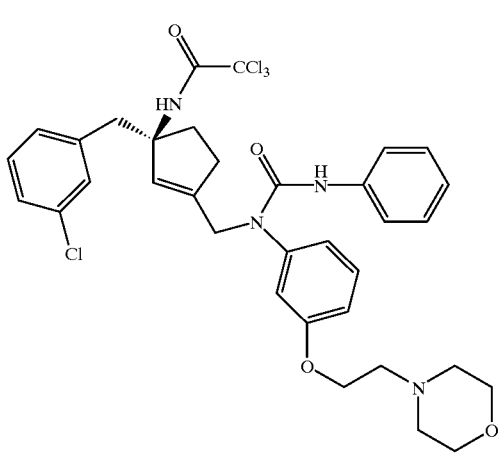

8. A pharmaceutical composition for treating disorders associated with the motilin receptor comprising an effective amount of a compound of claim 1 in association with one or more pharmaceutically acceptable carriers.

9. A method of treating disorders associated with the motilin receptor in humans comprising administering to a human in need of such treatment an effective amount of a compound of claim 1.

* * * * *